US008613695B2

(12) United States Patent
Von Ohlsen et al.

(10) Patent No.: US 8,613,695 B2
(45) Date of Patent: Dec. 24, 2013

(54) HIGHLY PRECISE AND LOW LEVEL SIGNAL-GENERATING DRIVERS, SYSTEMS, AND METHODS OF USE

(75) Inventors: Jon Von Ohlsen, Denver, CO (US); Dale Schoonover, Louisville, CO (US); Allen Braswell, Jr., Littleton, CO (US)

(73) Assignee: Applied Magnetics, LLC, Littleton, CO (US)

( * ) Notice: Subject to any disclaimer, the term of this patent is extended or adjusted under 35 U.S.C. 154(b) by 706 days.

(21) Appl. No.: 12/500,284

(22) Filed: Jul. 9, 2009

(65) Prior Publication Data
US 2010/0010288 A1      Jan. 14, 2010

Related U.S. Application Data

(60) Provisional application No. 61/079,670, filed on Jul. 10, 2008.

(51) Int. Cl.
*A61N 2/02*              (2006.01)
(52) U.S. Cl.
USPC ............................................... 600/9; 600/301
(58) Field of Classification Search
USPC .................. 600/9, 13, 14, 301; 128/897–899; 361/139–210
See application file for complete search history.

(56) References Cited

U.S. PATENT DOCUMENTS

| 781,448 | A | 1/1905 | McIntyre |
| 2,099,511 | A | 1/1934 | Caesar |
| 2,103,440 | A | 4/1934 | Weissenberg |
| 3,659,282 | A * | 4/1972 | Tada .............................. 345/611 |
| 3,738,369 | A | 6/1973 | Adams et al. |
| 3,890,953 | A | 6/1975 | Kraus et al. |
| 3,967,215 | A | 6/1976 | Bellak |
| 4,047,068 | A | 9/1977 | Ress et al. |
| 4,271,392 | A * | 6/1981 | Outram et al. ................ 324/115 |
| 4,323,056 | A | 4/1982 | Borrelli et al. |
| 4,524,079 | A | 6/1985 | Hofmann |
| 4,576,172 | A | 3/1986 | Bentall |

(Continued)

FOREIGN PATENT DOCUMENTS

| AU | B-45680/89 | 6/1990 |
| DE | 10157024 A1 | 5/2003 |

(Continued)

OTHER PUBLICATIONS

International Preliminary Report on Patentability mailed Jan. 20, 2011 for corresponding International Application No. PCT/US2009/050114.

(Continued)

*Primary Examiner* — Christine Matthews
*Assistant Examiner* — Joshua D Lannu
(74) *Attorney, Agent, or Firm* — Kilpatrick Townsend & Stockton LLP

(57) ABSTRACT

Apparatus and method for providing and using a highly precise and low level driver. In one described embodiment, a driver for a magnetic field generating device is provided, the driver including a first digital to analog converter and a second digital to analog converter; a differential amplifier configured to receive a first signal from the first digital to analog converter and receive a second signal from the second digital to analog converter and output a third signal; and an attenuator to configured to receive the third signal from the differential amplifier.

15 Claims, 7 Drawing Sheets

(56) References Cited

U.S. PATENT DOCUMENTS

| | | | |
|---|---|---|---|
| 4,611,599 A | 9/1986 | Bentall et al. | |
| 4,674,481 A | 6/1987 | Boddie et al. | |
| 4,723,536 A | 2/1988 | Rauscher et al. | |
| 4,889,526 A | 12/1989 | Rauscher et al. | |
| 5,019,076 A | 5/1991 | Yamanashi | |
| 5,021,941 A * | 6/1991 | Ford et al. | 700/71 |
| 5,088,976 A * | 2/1992 | Liboff et al. | 600/13 |
| 5,170,784 A | 12/1992 | Ramon et al. | |
| 5,198,181 A | 3/1993 | Jacobson | |
| 5,269,746 A | 12/1993 | Jacobson | |
| 5,366,435 A | 11/1994 | Jacobson | |
| 5,453,072 A | 9/1995 | Anninos et al. | |
| 5,470,846 A | 11/1995 | Sandyk | |
| 5,496,258 A | 3/1996 | Anninos et al. | |
| 5,691,324 A | 11/1997 | Sandyk | |
| 5,691,325 A | 11/1997 | Sandyk | |
| 5,697,883 A | 12/1997 | Anninos et al. | |
| 5,885,976 A | 3/1999 | Sandyk | |
| 5,964,759 A | 10/1999 | Yamanashi et al. | |
| 6,004,257 A | 12/1999 | Jacobson | |
| 6,022,479 A | 2/2000 | Smirnov | |
| 6,059,781 A | 5/2000 | Yamanashi | |
| 6,099,459 A | 8/2000 | Jacobson | |
| 6,155,966 A | 12/2000 | Parker | |
| 6,280,376 B1 | 8/2001 | Holcomb | |
| 6,287,614 B1 | 9/2001 | Peiffer | |
| 6,301,506 B1 | 10/2001 | den Boer et al. | |
| 6,458,071 B1 | 10/2002 | Jacobson | |
| 6,466,813 B1 | 10/2002 | Shukla et al. | |
| 6,488,617 B1 * | 12/2002 | Katz | 600/26 |
| 6,494,370 B1 * | 12/2002 | Sanchez | 235/454 |
| 6,527,697 B2 | 3/2003 | Bashford | |
| 6,579,375 B2 | 6/2003 | Beckett et al. | |
| 6,733,434 B2 | 5/2004 | Jacobson | |
| 6,804,558 B2 | 10/2004 | Haller | |
| 6,842,645 B2 | 1/2005 | Dalal | |
| 6,858,000 B1 | 2/2005 | Naraikin et al. | |
| 6,917,833 B2 | 7/2005 | Denker et al. | |
| 6,995,700 B2 | 2/2006 | Roger et al. | |
| 7,023,211 B2 | 4/2006 | Biglieri et al. | |
| 7,186,209 B2 | 3/2007 | Jacobson et al. | |
| 7,324,850 B2 | 1/2008 | Persen | |
| 7,395,117 B2 | 7/2008 | Mazar | |
| 8,049,504 B2 | 11/2011 | Findeklee | |
| 2002/0026228 A1 | 2/2002 | Schauerte | |
| 2004/0136489 A1 | 7/2004 | Takahashi et al. | |
| 2004/0181115 A1 | 9/2004 | Sandyk et al. | |
| 2005/0080459 A1 | 4/2005 | Jacobson et al. | |
| 2005/0283330 A1 | 12/2005 | Laraia et al. | |
| 2007/0004957 A1 | 1/2007 | Hilburg | |
| 2009/0094063 A1 | 4/2009 | Ennett | |
| 2010/0010288 A1 | 1/2010 | Ohlsen et al. | |
| 2010/0057655 A1 | 3/2010 | Jacobson et al. | |
| 2010/0072996 A1 | 3/2010 | Jacobson et al. | |
| 2010/0298624 A1 | 11/2010 | Becker | |

FOREIGN PATENT DOCUMENTS

| | | |
|---|---|---|
| EP | 371 504 | 1/1997 |
| GR | 1003262 | 11/1999 |
| WO | WO 91/06341 | 5/1991 |
| WO | WO 92/03185 | 3/1992 |
| WO | WO 95/31939 | 11/1995 |
| WO | WO 97/46244 | 12/1997 |
| WO | WO 99/13884 | 3/1999 |
| WO | WO 00/13749 | 3/2000 |
| WO | WO 01/15775 | 3/2001 |
| WO | WO 03/017061 A2 | 2/2003 |
| WO | 2007051419 A1 | 3/2006 |

OTHER PUBLICATIONS

International Preliminary Report on Patentability mailed Mar. 10, 2011 for corresponding International Application No. PCT/US2009/054803.

International Preliminary Report on Patentability mailed Mar. 10, 2011 for corresponding International Application No. PCT/US2009/055183.

International Search Report and Written Opinion mailed Nov. 5, 2009 corresponding to PCT Patent Application No. PCT/US2009/054803.

International Search Report and Written Opinion mailed Nov. 6, 2009 corresponding to PCT Patent Application No. PCT/US2009/050114.

Jacobson, J. I. and Yamanashi, W. S., "A Possible, Physical Mechanism in the Treatment of Neurologic Disorders with Externally Applied Pico Tesla Magnetic Fields," Physiol. Chem. Phys & Med. NMR, 1994 26:287-297.

Jacobson, J.I., "Jacobson Resonance: The Quantum-Mechanical Basis for a Novel Radiological Approach to Treating Cancer and Aids," Frontier Perspectives, Fall/Winter 1996, 6(1):17-26.

Sandyk, R., "Alzheimer's Disease: Improvement of Visual Memory and Visuoconstructive Performance by Treatment with Picotesla Range Magnetic Fields," Intern. J. Neuroscience, 1994, 76:185-225.

Sandyk, R., "Clinical Case Report Successful Treatment of Multiple Sclerosis with Magnetic Fields," Intern. J. Neuroscience, 1992, 66:237-250.

Sandyk, R., "Clinical Case Report Magnetic Fields in the Treatment of Parkinson's Disease," Intern. J. Neuroscience, 1992, 63:141-150.

IEEE, "IEEE Xplore 2.0 User Guide," Nov. 11, 2006, (website) http://ieeexplore.ieee.org/otherfiles/x20_guidefull.pdf, pp. 1-76.

Canadian Intellectual Property Office, Office Action, Application No. 2,730,089, dated Sep. 13, 2012.

Adey, W.R., "Physiological Signaling Across Cell Membranes and Cooperative Influences of Extremely Low Frequency Electromagnetic Fields," *Biological Coherence and Response to External Stimuli*, Herbert Frohlich Ed., Springer-Verlag, 1988, 148-170.

Adey, W.R., "Tissue Interactions with Nonionizing Electromagnetic Fields," *Physiological Reviews*, 1981, 61(2): 435-514.

Anninos, P.A. et al., "The Biological Effects of Magnetic Stimulation in Epileptic Patients," *Panminerva Medica*, 1999, 41(3): 207-215.

Anninos, P.A. et al., "Magnetic Stimulation in the Treatment of Partial Seizures," *Intern. J. Neuroscience*, 1991, 60: 141-175.

Beall, P.T. et al., "Distinction of Normal, Preneoplastic, and Neoplastic Mouse Mammary Primary Cell Cultures by Water Nuclear Magnetic Resonance Relaxation Times," *JNCI.*, 1980, 64(2): 335-338.

Bistolfi, F., "Biostructures and Radiation Order Disorder," *Edizioni Minerva Medica, Corso Bramante 83/85*-Torino, 1991, 61-92, 261.

Cheng, D.K., *Field and Wave Electromagnetics*, Addison Wesley Publishing Company, 1983, 255-261, 569-576.

Clegg, J.S., "Intracellular Water and the Cytomatrix: Some Methods of Study and Current Views," *The Journal of Cell Biology*, 1984, 99(1): 167-171.

Clegg, J.S., "Intracellular Water, Metabolism and Cell Architecture; Part 2," *Coherent Excitations in Biological Systems*, Herbert Frohlich Ed., Springer-Verlag, 1983, 162-177.

Clegg, J.S., "Properties and Metabolism of the Aqueous Cytoplasm and Its Boundaries," *The American Physiological Society*, 1984, R133-R151.

Cohen, D., "Magnetoencephalography: Detection of the Brain's Electrical Activity with a Superconducting Magnetometer," *Science*, 1971, 175: 664-666.

Cremer-Bartels, G., "Influence of Low Magnetic-Field-Strength Variations on the Retina and Pineal Gland of Quail and Humans," *Graefe's Archive Ophthalmology*, 1983, 220: 248-252.

Egan, T.F. et al., "Molecular Basis of Contrast in MRI," *Cell Function and Disease*, Candeo et al, (eds), Plenum Press, New York and London, 1988, 405-413.

Eichhorn, G.L., "Aging, Genetics and the Environment: Potential Errors Introduced Into Genetic Information Transfer by Metal Ions," *Mechanisms of Ageing and Developments*, 1979, 9: 291-301.

Hazlewood, C.F., "Implications of Cellular Water in Health and Disease," Second Annual Advanced Water Sciences Symposium, Dallas, TX, Oct. 4-6, 1996, 1-5.

Hazlewood, C.F., "A Role for Water in the Exclusion of Cellular Sodium—Is a Sodium Pump Needed?" Cardiovascular Diseases, *Bulletin of the Texas Head Institute*, 1975, 2(1): 83-104.

(56) References Cited

OTHER PUBLICATIONS

Hazlewood, C.F., "A View of the Significance and Understanding of the Physical Properties of Cell-Associated Water," *Cell-Associated Water*, Academic Press, Inc., 1979, 165-259.

Hazlewood, C.F "Diffusion of Water in Tissues and MRI," *Magnetic Resonance in Medicine*, 1991, 19: 214-216.

Jacobson, J.I., "Jacobson Resonance: The Coupling Mechanism for Weak Electromagnetic Field Bioeffects, and a New Way to Approach Magneto Therapy," *Panminerva Medica*, 1994, 36(1): 34-41.

Jacobson, J.I., "Exploring the Potential of Magneto-Recrystallization of Genes and Associated Structures with Respect to Nerve Regeneration and Cancer," *Int. Journal of Neuroscience*, 1992, 64(1-4): 153-165.

Jacobson, J.I., "Is the Fusion Process the Basis for Growth, Repair, and Aging?" *Panminerva Medica*, 1990, 32(3): 132-140.

Jacobson, J.I. et al., "Pico Tesla Range Magnetic Fields Tested in Four Site, Double Blind Clinical Study for Treatment of Osteoarthritic Knees," *Gazzetta Medica Italiana—Arch. Sci. Med.*, 2001, 160: 1-21.

Jacobson, J.I., "Jacobson Resonance: The Quantum-mechanical Basis for a Novel Radiological Approach to Treating Cancer and AIDS," *Frontier Perspectives*, 1996, 6(1): 17-26.

Jacobson, J.I., "Jacobson Resonance is the Basis From Which to Evaluate Potential Hazard and Therapeutic Benefit from Extrinsic Magnetic Fields," *Panminerva Medica*, 1993, 35(3): 138-148.

Jacobson, J.I. "A Look at the Possible Mechanism and Potential of Magneto Therapy," *Journal of Theoretical Biology*, 1991, 149(1): 97-119.

Jacobson, J.I., "Physics in Medicine: A Potential Unfolding in the Radiological Sciences," *Panminerva Medica*, 1996, 39(2): 111-127.

Jacobson, J.I., "Pineal-Hypothalamic Tract Mediation of Picotesla Magnetic Fields in the Treatment of Neurological Disorders," *Panminerva Medica*, 1994, 36(4): 201-205.

Jacobson, J.I., "A Theoretical Look at Gravity in the Human Cell: Its Role in Normal Cell Division as Well as Neoplasia," *Panminerva Medica*, 1992, 34(3): 96-106.

Jacobson, J.I. et al., "A Possible, Physical Mechanism in the Treatment of Neurologic Disorders with Externally Applied Pico Tesla Magnetic Fields," *Physiol. Chem. Phys. & Med. NMR*, 1994, 26: 287-297.

"Jacobson Resonance Enterprises, Inc. Announces Research Findings in Breast Cancer Cells from the College of Veterinary Medicine at Mississippi State University," press release Apr. 30, 2004.

Kasturi, S.R., "Study of Anisotropy Nuclear Magnetic Resonance Relaxation Times of Water Protons in Skeletal Muscle," *Biophys. J.*, 1980, 30: 369-381.

Kasturi, S.R., "The Nature and Origin of Chemical Shift for Intracellular Water Nuclei in Artemia Cysts," *Biophys. J.*, 1987, 52: 249-256.

Kasturi, S.R., "Intracellular Water in *Artemia cysts* (Brine Shrimp) Investigations by Deuterium and Oxygen-17 Nuclear Magnetic Resonance," *Biophys. J.*, 1990, 58: 483-491.

Lawrence, A.F. et al., "Nonlinear Wave Mechanisms in Interactions between Excitable Tissue and Electromagnetic Fields," *Neurological Research*, 1982, 4(1-2): 115-153.

Mikesell, N.D., "Structured Water: Its Healing Effects on the Diseased State," web-page at http://www.naturesalternatives.com/lc/mikesell.html as created on the internet Feb. 27, 1999.

"Oklahoma University researchers report dramatic growth effects of bean sprouts using Jacobson resonation," presented to the Indian Medical Association, Calcutta, India, 2002.

Qin, C. et al., "Effects on Rats of Low Intensity and Frequency Electromagnetic Field Stimulation on Thoracic Spinal Neurons Receiving Noxious Cardiac and Esophageal Inputs," Neuromodulation, 8(2): 79-87.

Reuss, S., "Different Types of Magnetically Sensitive Cells in the Rat Pineal Gland," *Neuroscience Letters*, 1983, 40: 23-26.

Rorschach, H.E. et al., "Diffusion of Water in Biological Tissues," *Scanning Microscopy Supplement*, 1991, 5: S1-S9.

Sandyk, R., "Alzheimer's Disease: Improvement of Visual Memory and Visuoconstructive Performance by Treatment with PicoTesla Range Magnetic Fields," *Intern. J. Neuroscience*, 1994, 76: 185-225.

Sandyk, R., "Clinical Case Report: Magnetic Fields in the Treatment of Parkinson's Disease," *Intern. J. Neuroscience*, 1992, 63: 141-150.

Sandyk, R., "Clinical Case Report: Successful Treatment of Multiple Sclerosis with Magnetic Fields," *Intern. J. Neuroscience*, 1992, 66: 237-250.

Saxena, A. et al, "Hypothetical Mathematical Construct Explaining the Mechanism of Biological Amplification in an Experimental Model Utilizing PicoTesla (PT) Electromagnetic Fields," *Medical Hypotheses*, 2003, 60(6): 821-839.

Scherlag, B.J. at al., "The Application of Low-Level Electromagnetic Fields to the Autonomic Nerve Inputs to the Heart: Effects on Heart Rate and Atrioventricular Conduction," abstract presented at annual meeting of the American Institute of Stress, in Hawaii, 2000.

Scherlag, B.J. et al., "Magnetism and Cardiac Arrhythmias," *Cardiology in Review*, 2004, 12(2): 85-96.

Scherlag, B.J. et al., "Use of Low-Level Electromagnetic Fields and Vago-Sympathetic Stimulation to Detect and Induce the Paroxysmal Atrial Fibrillation Syndrome," abstract presented at annual meeting of the American Institute of Stress, in Hawaii, 2000.

Seitz, P.K. et al., "Proton Magnetic Resonance Studies on the Physical State of Water in *Artemia cysts,*" *The Brine Shrimp Artemia*, 1980, 2: 545-554.

Trostel, C.T., DVM, et al., "Effects of Pico-Tesla Electromagnetic Field Treatment on Wound Healing in Rats," *Am.J.Veterinary Res.*, 2003, 64(7): 845-854.

Wangsness, R.K., *Electromagnetic Fields*, John Wiley & Sons, Chapter 14, 1986, 225-236.

Welker, H.A., "Effects of an Artificial Magnetic Field on Serotonin N-Acetyltransferase Activity and Melatonin Content of the Rat Pineal Gland," *Exp. Brain. Res.*, 1983, 50: 426-432.

Yamanashi, W. et al., "The Effect of Low-Level Electromagnetic Fields on a Simple Model of Osmosis, in Vitro," abstract presented at annual meeting of the American Institute of Stress, in Hawaii, 2000.

State Intellectual Property Office of the People's Republic of China, Notification of the First Office Action, Application No. 200980135319, dated Mar. 26, 2013.

Patent Cooperation Treaty, International Search Report and Written Opinion, International Application No. PCT/US13/31563, mailed Jun. 5, 2013.

\* cited by examiner

HIGHLY PRECISE AND LOW LEVEL SIGNAL-GENERATING DRIVERS, SYSTEMS, AND METHODS OF USE

CROSS-REFERENCES TO RELATED APPLICATIONS

This patent application claims priority to: U.S. Provisional Patent Application No. 61/079,670, entitled "Highly Precise and Low Level Signal-Generating Drivers, Systems, and Methods of Use" filed Jul. 10, 2008, the entirety of which is hereby incorporated by reference.

FIELD OF THE INVENTION

The present invention relates to drivers for providing a signal in order to generate a magnetic field. In particular, this invention relates to a highly precise and low-level self-compensating signal-generating driver for providing a signal in order to generate a highly precise and accurate magnetic field.

BACKGROUND

Magnetic therapy is not new. For hundreds of years, magnets have been used to treat a wide variety of medical conditions. Today, electromagnetic (i.e., devices that use an electric current to produce a magnetic field) therapy is garnering increasing public awareness as a natural or complementary alternative for the treatment of illness and chronic pain. In recent years, the impact of treatment with electromagnetic fields on physical ailments has been presented in peer-reviewed scientific studies. More studies are underway as the interest in electromagnetic therapies escalates. As a result, the electromagnetic products industry is growing rapidly.

Electromagnetic therapy systems may be used to treat a variety of conditions and ailments through the application of a magnetic field to a human or other subject. The impressed magnetic field may range widely depending on the therapeutic method and the condition being treated. For example, a magnetic flux density of 2 Teslas may be used in transcranial magnetic stimulation therapy (TMS), while fields as low as the pico-Tesla range may be applied for conditions such as Parkinson's disease and epilepsy according to the Jacobson magnetic therapy protocol, as described in U.S. Pat. Nos. 5,269,746 and 5,366,435.

Many electromagnetic therapy systems produce low-level magnetic fields in the micro-Tesla range and below, over frequencies of a few hundred Hertz, down to DC. These magnetic fields are typically generated using magnetic coils that are driven by low-current levels (e.g., micro-amperes and lower) created by drivers which include an off-the-shelf signal generator in series with a manual attenuator, (e.g., a manual switch-box containing discrete resistors). The magnetic coil used may be a Helmholtz coil, which produces an especially uniform field, although many other coil configurations are possible (e.g., a solenoid, a poloidal coil, a toroid etc.).

A limitation present in known systems is a lack of precision and accuracy due to electronic errors resulting from non-linearity and stray AC and DC offsets. Non-linearity and stray AC and DC offsets can be caused by using commercial-grade and consumer-grade components. A known way to limit non-linearity and stray AC and DC offsets may be to use laboratory-grade components. However, laboratory-grade components are much more expensive than commercial or consumer-grade components.

SUMMARY

Embodiments of the present invention provide apparatuses and methods for providing and using a highly precise and low level driver. One embodiment is a driver for a magnetic field generating device, comprising: a first digital to analog converter and a second digital to analog converter; a differential amplifier configured to receive a first signal from the first digital to analog converter and receive a second signal from the second digital to analog converter and output a third signal; and an attenuator to configured to receive the third signal from the differential amplifier.

These embodiments are mentioned not to limit or define the invention, but to provide examples of embodiments of the invention to aid in understanding thereof. Embodiments are discussed in the Detailed Description, and further description of the invention is provided there. Advantages offered by the various embodiments of the present invention may be further understood by examining this specification.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Figure 1:
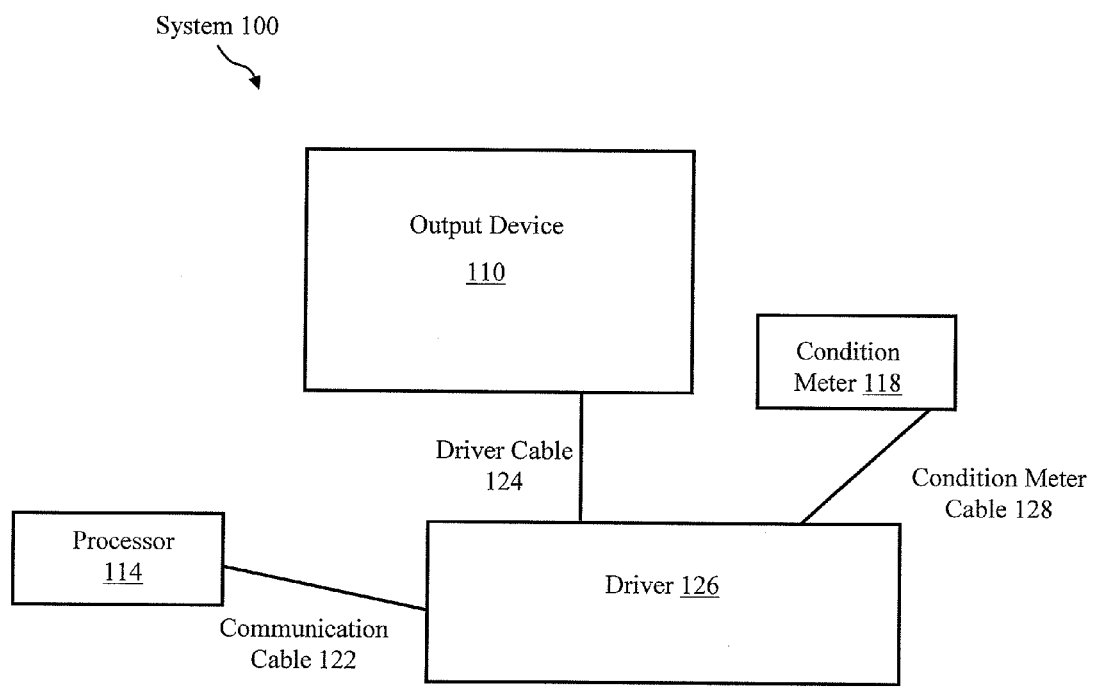
FIG. 1 is a functional block diagram illustrating a system according to one embodiment of the present invention.

Embodiments of the present invention provide apparatuses, systems, and methods for providing and using a highly precise driver. In some embodiments, the driver may be used to drive a magnetic therapy device. In one embodiment, the device is a highly precise low level magnetic therapy driver. In further embodiments, the driver may be used for other purposes.

In certain embodiments, the driver provides a signal to an output device. In one embodiment, the output device provides a magnetic field. In a further embodiment, the output device may comprise a coil. In a further embodiment, the output device may comprise a plate.

In one embodiment, through program code stored on a computer readable medium and executed by a processor, an operator may control the amplitude and frequency of low-level signals produced by the driver. The present invention also minimizes electronic errors due to non-linearity and stray AC and DC offsets. A need exists to minimize electronic errors in a way that does not require using expensive laboratory-grade components. Embodiments of the present invention solve this problem, for example, by computing correction factors which may include a gain error correction (AC calibration) and an offset correction (DC calibration). These correction factors may then be used to compute the amount of current to direct the driver to produce.

There is a further need presently felt in the art for a driver that is both accurate and precise. Embodiments of the present invention meet this need in a number of ways. For example, embodiments of the present invention provide a driver that is capable of adjusting its output based on inputs from a device to monitor output and/or as the ambient environment. In one embodiment, the device is a magnetometer that senses the ambient magnetic environment. Embodiments of the present invention may further provide a low-level signal output substantially proportional to the ambient temperature. Additionally, embodiments of the present invention provide a system that incorporates sensors such that the driver output is based at least in part on signals received from the sensors. Further, certain embodiments of the present invention provide a driver that can be located near the output device, and thereby minimize the length of the cable to the output device.

In some embodiments of the present invention, a driver for a magnetic field generating device is provided. In some embodiments, the driver comprises components that provide the driver with an ability to reduce variations and instability in the generated magnetic field. Examples of such components are identified and described herein.

In some embodiments of the present invention, a driver for a magnetic field generating device is provided. In some embodiments, the driver comprises a first digital to analog converter and a second digital to analog converter. In some embodiments, the driver further comprises a differential amplifier configured to receive a first signal from the first digital to analog converter and receive a second signal from the second digital to analog converter and output a third signal. In some embodiments, the driver further comprises an attenuator to configured to receive the third signal from the differential amplifier. In some embodiments, the first and second signals are used to calibrate the driver.

In some embodiments, the driver comprises at least one digital to analog converting device. The digital to analog converting device may be for example, a digital to analog converter circuit capable of converting a digital electronic signal to an analog electronic signal. In some embodiments the digital to analog converting circuit may be an integrated component. One embodiment of the present invention comprises a first digital to analog converter (hereinafter "DAC-1") and a second digital to analog converter (hereinafter "DAC-2"). In some embodiments additional digital to analog converters may be used. For example, in some embodiments three or more digital to analog converters may be used. In some embodiments, DAC-1 and DAC-2 produce signals. In a further embodiment, the signals from both DAC-1 and DAC-2 may be used to calibrate the driver. Also, the signals from DAC-1 and DAC-2 may be used to provide a therapeutic dose of magnetic field. Furthermore, the signals from DAC-1 and DAC-2 may be used may be used for any other purpose known in the art.

In some embodiments, the driver comprises a differential amplifier. In some embodiments, the differential amplifier may be for example an operational amplifier circuit. In other embodiments, the differential amplifier may be circuit comprising transistors such as Field Effect Transistors or Bipolar Junction Transistors. The differential amplifier may be configured to receive input from the digital to analog converters. For example, in some embodiments, the differential amplifier may be configured to receive input from the first and second digital to analog converters (e.g. DAC-1 and DAC-2). In some embodiments, the differential amplifier provides an output signal. This output signal may comprise a signal substantially approximating the difference between the signals received from DAC-1 and DAC-2. In some embodiments, the driver uses the signal from the differential amplifier to control the magnetic field generating device. Also, the signal may be used to provide a therapeutic dose of magnetic field. Furthermore, the signals from DAC-1 and DAC-2 may be used for any other purpose known in the art.

In some embodiments, the driver comprises an attenuator. The attenuator may receive a signal from one or more sources. In one embodiment, the attenuator receives a signal from the differential amplifier. In a further embodiment, the attenuator may generate an output signal. In one embodiment, the attenuator's output signal may be used to control the magnetic field generating device.

In some embodiments, the driver further comprises a voltage reference source. The voltage reference source may be used to provide a constant voltage. In one embodiment the voltage reference source is capable of providing voltage to one or more components. In some embodiments, the voltage reference source may provide output to one or more relay devices. In some embodiments, the voltage reference source may be capable of providing voltage to a signal generator. In further embodiments, the voltage reference source may be capable of providing voltage to various other devices known in the art.

In some embodiments, the driver further comprises a signal generator. The signal generator may be used to provide an electronic signal. The signal may comprise a sine wave, square wave, or any other waveform. In one embodiment, the signal generator may provide the signal to one or more devices. In some embodiments, the signal generator may be capable of receiving commands. The commands may be received via a system bus, or any other communication means—wired or wireless—known in the art.

In some embodiments, the driver comprises at least one relay device. In some embodiments, the driver further comprises at least one relay device connected to at least one of the digital to analog converters. In some embodiments the relay may be for example a latching relay or a solid state relay. In other embodiments, the relay device may be an H-Bridge or similar circuit. The relay device(s) may be connected to at least one of the digital to analog converters. In some embodiments, the relay device(s) may be capable of receiving a signal as input and providing a signal as output. In some embodiments, the signals may include commands. The signal may be provided by one or more sources, according to various embodiments. In one embodiment, one or more relay devices may receive a signal as input from the signal generator. In one embodiment, one or more relay devices may receive a signal from a voltage reference source. In other embodiments, one or more relay devices may receive one or more signals from various sources. Further, the relay device(s) may output a signal to one or more destinations, according to various embodiments.

In one embodiment, a relay device is used to provide output from the signal generator to a destination device. The destination device, in some embodiments, may be the first and/or second digital to analog converter.

In one embodiment, a relay device is used to provide output from the voltage reference source to a destination device. The destination device, in some embodiments, may be the second digital to analog converter.

In one embodiment of the present invention, at least one relay device is used to relay output from the voltage reference source to the second digital to analog converter. In another embodiment of the present invention, at least one relay device is used to relay output from the signal generator to the first digital to analog converter.

In one embodiment, the driver further comprises a controller. In some embodiments the controller comprises a processor. In some embodiments, the controller may comprise a microcontroller, microprocessor, Field Programmable Gate Array (FPGA), Programmable Interrupt Controller (PIC), Programmable Logic Controller (PLC), or any other controller known in the art. In some embodiments, the controller may be capable of receiving signals comprising data from one or more devices. In some embodiments, the controller may be capable of providing signals comprising information, such as one or more commands, to one or more devices. The controller may receive and/or provide such signals by using various communication means known in the art—wired and/or wireless. In one embodiment, the controller may communicate to one or more devices in the system using a system bus.

Drivers known in the art produce magnetic fields that have some degree of variation. The variations in actual magnetic field are primarily a function of drive current and coil changes. Thus, the factors that affect the current through a particular coil need to be understood and controlled. One embodiment meets this need by providing a driver that is capable of providing output that is accurate and/or precise. The coil dimensions including length may be affected by temperature and this can be used to control the drive signal. Typical variations in actual magnetic field would be expected at greater than 10% unless very specific design mitigations are taken. The relationship between the current flow in a particular coil and the resultant magnetic field can be used to predict the (ideal) generated magnetic field. In one embodiment, the electronics providing the signal to the coils can be accurate to 0.01% over the full range of drive amplitudes. For example, in some embodiments, the driver is capable of providing an output that varies by less than 1%, or 2%, or 5%, or 10%, or any variation known in the art, from the expected output.

In other embodiments, the present invention comprises methods of providing a magnetic field. In some embodiments, the magnetic field may be suitable for magnetic therapy. The present invention may provide the magnetic field by using one or more embodiments of the driver described herein. In some embodiments, the driver comprises components that provide the driver with an ability to reduce variations in the magnetic field used to drive a magnetic therapy generating device.

In certain embodiments, the driver may use the signal received from the one or more digital to analog converters to provide output to the magnetic therapy generating device. In further embodiments, the driver may combine the signal provided by the one or more digital to analog converters with an AC calibration factor and/or a DC calibration factor in order to calculate the signal to be provided. In one embodiment, after determining the signal, the driver may provide the determined signal as output to the output device.

In yet other embodiments, the present invention comprises a system for providing a magnetic field suitable for magnetic therapy. The system may comprise one or more embodiments of the driver, as described herein.

In one embodiment, the system further comprises coils for generating the magnetic field. The coils may receive an electrical signal from one or more embodiments of the driver, described above. In some embodiments, the system may generate the magnetic using a device other than a coil. For example in some embodiments, the magnetic field may be generated using plates. In such an embodiment, the plate may comprise metal. In other embodiments, the plate may comprise a composite material. In other embodiments, the magnetic field may be generated using some other means known in the art.

In one embodiment, the system further comprises one or more sensors. The one or more sensors may have the capability to monitor physical parameters of a subject that is a recipient of the magnetic field. For example, in some embodiments, the sensors may be configured to measure one or more of: temperature, heart rate, or blood pressure. In a further embodiment, the one or more sensors may have the capability to monitor any number of parameters of various types. Further, the one or more sensors may have the capability to provide data via a variety of communication means known in the art—wired and/or wireless.

In one embodiment, the system further comprises a magnetometer. The magnetometer may have the capability to monitor an ambient magnetic field. In a further embodiment, the magnetometer may have the capability to monitor a magnetic field provided by the system. Further, the magnetometer may have the capability to provide data via a variety of communication means known in the art—wired and/or wireless. In a further embodiment, the magnetometer may communicate data to one or more components of the system so that the system may adapt its output to account for the ambient magnetic field.

FIG. 1 is a functional block diagram illustrating system 100 according to one embodiment of the present invention. While a specific embodiment of the present invention is demonstrated by system 100, many other configurations are possible.

Thus, as illustrated in the embodiment of FIG. 1, system 100 may comprise a driver 126 of the present invention. System 100 may comprise an output device 110 in communication with the driver 126. In one embodiment, the output device 110 comprises a coil assembly. System 100 may further comprise a processor 114. Also, system 100 may comprise a condition meter 118 to monitor one or more conditions. The condition meter may be located in close proximity to the output device 110. In one embodiment, the condition meter 118 is a magnetometer. For example, the condition meter 118 may monitor ambient conditions, such as the ambient magnetic field. In various embodiments, the condition meter 118 can measure the level, duration, and strength of various signals and conditions, including magnetic fields. System 100 may further comprise a communication cable 122. Also, system 100 may comprise a driver cable 124. In one embodiment, the driver 126 is in communication with the processor 114 via a communication cable 122. In one embodiment, the driver 126 is in communication with the output device 110 via the driver cable 124. Also, system 100 may comprise a condition meter cable. In one embodiment, the condition meter cable 128 is in communication with the condition meter 118 and the driver 126. In further embodiments, the system comprises other components (not pictured in FIG. 1). For example, the system 100 may comprise sensors, for example system 100 may comprises sensors including, but not limited to pressure, temperature, humidity, heart rate, blood pressure, electroencephalograph (EEG), and electrocardiograph (EKG) sensors. Also, the system 100 may comprise a coil housing.

Also, the system 100 may comprise a compensation network. For example, in one embodiment Compensation network may comprise a resistor and capacitor network that is matched to the impedance of the coil assembly, and used to negate the reactance of the coil over a small range of frequencies, for example, from 0.1 Hz to 500 Hz. In some embodiments, the coil assembly may be wired in parallel with the compensation network, thereby providing a standardized impedance, with minimum variation between individuals in production lots. As a result of this impedance matching, alternative sets of coil assembly can be used in magnetic therapy system 100 without the need for recalibration.

The output device 110 may comprise any device capable of receiving input from the driver 126. For example, the output device 110 may comprise a solenoid, a Maxwell coil, a poloidal coil, or other output device. In various embodiments, the output device 110 may comprise any magnetic coil configuration that produces a uniform magnetic field proportional to the electric current within its magnetic coils, over a volume sufficient to accommodate a magnetic therapy subject. In one embodiment, the output device 110 may include a Helmholtz coil. For example, in one embodiment, the output device 110 may include two co-axial 7-foot diameter coils spaced 3.5-feet apart, each coil having 30-turns of 30-gauge solid-core copper wire (not shown). However, other dimension coils with different numbers of turns and construction may be used. The output device 110 may be wired in parallel with the compensation network. Also, the output device 110 may be electrically connected to the driver 126. For example, in one embodiment, the output of the driver is provided to the driver cable 124. The driver cable 110 may be electrically connected to the output device 110. In one embodiment, the output device 110 and driver 126 are housed within the chassis of the coil housing.

In certain embodiments, the system may comprise one or more sensors, including, for example, biometric sensors that measure a variety of physical parameters. The sensors may measure physical parameters including physiological functions of subjects before, during, and after receiving magnetic therapy treatment in the system 100. Examples of physical parameters may include, but are not limited to pressure, temperature, humidity, heart rate, blood pressure, electroencephalograph (EEG), and electrocardiograph (EKG) sensors. In one embodiment, the sensors may be electrically connected to the driver 126 through a variety of communication means. In alternative embodiments, the sensors may be connected by both wired and wireless means. For example, a wired connection may include wired communication standards such as USB and RS232. Alternatively, the wireless connection may include Bluetooth (IEEE 802.15) and/or WiFi (IEEE 802.11). In one embodiment, the use of the sensors may allow the processor 114 to integrate sensor feedback into the control of the driver 126, such that the output produced by the driver is based, in part, on signals received from sensors.

In certain embodiments, the system may comprise a processor 114. The processor 114 may comprise a standard processing device, such as a personal computer, laptop, or host computer, capable of running the system control software for operating the driver 126. In other embodiments, the processor may comprise, for example, a microprocessor, an application-specific integrated circuit (ASIC), a state machine, Field Programmable Gate Array (FPGA), Programmable Logic Controller (PLC), Programmable Interrupt Controller (PIC), or other integrated component.

The processor 114 may further comprise a computer-readable medium capable of storing computer-executable instructions. Embodiments of computer-readable media may comprise, but are not limited to, an electronic, optical, magnetic, or other storage device, transmission device, or other device that comprises some type of storage and that is capable of providing a processor with computer-readable instructions. Other examples of suitable media may comprise, but are not limited to, a floppy disk, compact disc read-only memory (CD-ROM), digital video disc (DVD), magnetic disk, memory chip, read-only memory (ROM), random access memory (RAM), programmable read-only memory (PROM), field programmable read-only memory (FPROM), erasable programmable read-only memory (EPROM), electrically erasable programmable read-only memory (EEPROM), an application specific integrated circuit (ASIC), a configured processor, all optical media, all magnetic tape or other magnetic media, or any other medium from which a computer processor can read instructions. Also, various other forms of computer-readable media may be embedded in devices that may transmit or carry instructions to a computer, including a router, private or public network, or other transmission device or channel, both wired and wireless. The instructions may comprise code from any suitable computer programming language, including, for example, COBOL, C, C++, C##®, Visual Basic®, Java™, Python®, and Perl™.

In one embodiment, the processor 114 may be connected to a network connection, such as a local area network (LAN), wide area network (WAN), server, or Internet connection, for download or storage of data from another computer, host, or centralized server. In certain embodiments, the tasks or functions of the processor 114 may be completed with a single computer. In other embodiments, the tasks or functions of the processor 114 may be completed by more than one computer. In further embodiments, the computers may be communicatively connected to one another, for example, by a network connection. In the course of its operation, the processor 114 may communicate operational commands, such as normal operation on/off, alternating current (AC) calibration, direct current (DC) calibration, and other commands to the driver 126. For example, in some embodiments the communication cable 122 is used to communicate commands from the processor to the driver 126. In other embodiments, the processor 114 may also receive various data from other components of the system. For example, the processor 114 may receive a signal comprising data, including temperature data, from a sensor, such as the T-sense 226 (depicted in FIG. 3). In a further embodiment, the processor 114 may also receive signals comprising data, such as magnetic data, from the condition meter 118. In some embodiments, the processor 114 may receive signals comprising data via the communication cable 122 by means of the driver 126, which may allow the processor 114 to respond to external (sensor) inputs in a real-time feedback/control system loop.

In a some embodiments, the processor 114 may receive signals from a user interface. In some embodiments, the user interface may include a keyboard. In some embodiments, the user interface may include a mouse. In some embodiments, the user interface may include a monitor or other display; in such an embodiment, the display may further comprise a touch-screen display. In some embodiments, the monitor may be capable of displaying a graphical user interface (GUI). In some embodiments, the GUI may enable the operator of the magnetic therapy system 100 to initiate normal operation. In some embodiments, the GUI may enable the operator to select one or more magnetic therapy options. In further embodiments, the GUI may enable the operator to initiate AC and/or DC calibration modes as described herein. For example, an operator may enter therapeutic parameters using the processor 114, via the processor's GUI in a variety of ways, for example, by condition to be treated, by a regime code, or by the entry of specific magnetic waveform parameters, such as waveform type (e.g., sinusoidal, square, sawtooth), amplitude (e.g., 0.032 micro-gauss, 0.017 micro-gauss, 0.075 micro-gauss) and frequency (e.g., 0.3 Hz, 0.8 Hz, 5 Hz, 10 Hz). After the operator enters the therapeutic parameters, the processor 114 may transmit a signal comprising the specific electric waveform parameters required, such as waveform type (e.g., sinusoidal, square, sawtooth), amplitude (e.g., 0.017 micro-gauss, 0.032 micro-gauss, 0.075 micro-gauss) and frequency (e.g., 0.3 Hz, 0.8 Hz, 5 Hz, 10 Hz) to the driver 126. In one embodiment, the processor 114 may transmit a signal comprising the specific electric waveform parameters to a microcontroller within the driver 126. In further embodiments, the processor 114 may transmit a signal comprising the specific electric waveform parameters via the communication cable 122. In some embodiments, the processor 114 is electrically connected to the driver 126 via the communication cable 122.

In some embodiments, the processor 114 may employ shielding elements that prevent electromagnetic radiation emanating from the processor 114 from interfering with the operation of the system 100. In some embodiments, a chassis exterior having 20-thousands (0.02") steel, or 10-thousands (0.01") mu metal may serve this purpose. In other embodiments another type of electromagnetic shielding may be used. For example, in some embodiments processor 114 may employ shielding comprising aluminum, stainless steel, or some other metal.

In one embodiment in which the output device 110 comprises a coil assembly, the coil housing may be a chassis that provides an enclosure for the output device 110. The coil housing may be constructed of a non-magnetic and non-conductive housing such as fiberglass or composite, to minimize magnetic interference with the output device 110. In various embodiments, the coil housing may be of a variety of sizes and shapes, and thus may be capable of accommodating different sized and shaped output devices 110. In addition, the coil housing can also provide a means of easily changing the position and orientation of the output device 110. In one embodiment, the output device 110 may include an articulated mechanical arm for use with smaller coils.

In one embodiment, the condition meter 118 is a magnetometer. In an embodiment in which the output device 110 comprises a coil assembly, the condition meter may be a magnetic sensor that measures the magnetic field between the coils of the output device 110. Magnetic interference from environmental sources, both natural and made-made, can negatively impact the accuracy of magnetic therapy systems. The Earth's magnetic field, for example, is in the order of 30 to 60 micro-Tesla. In addition, the U.S. National Institute of Health (NIH) estimates that the average ambient magnetic field in the U.S. due to various electrical and electronic sources is approximately 0.2 micro-Tesla. Personal computer monitors alone, for example, can produce magnetic fields of 0.2 micro-Tesla at 30 cm (about 1 foot) from the front surface of the monitor. Other electric devices, particularly those comprising electric motors, may generate much larger ambient magnetic fields. These ambient magnetic fields—including those from power lines and/or electrical equipment—can interfere with low-level magnetic fields, such as those generated by a magnetic therapy system.

However, if the ambient magnetic field is measured, its interference may be reduced by various means. As a result, a driver capable of adapting its output to account for the ambient magnetic environment is needed. In addition to measuring the ambient magnetic field, there may be a further need to integrate other sensors, such as biometric sensors, such that the output of the driver is informed by sensor inputs. Embodiments of the present invention meet these needs in a number of ways, some examples of which are described herein.

In certain embodiments, the condition meter 118 is a magnetometer capable of measuring low-level magnetic fields, including those in the nano-Tesla (nT) range (0.1 nT to 100 nT, at 5-10%), and of resolving the magnitude these fields into three orthogonal components (x-y-z). In one embodiment, the condition meter 118 includes the GEM GSMP-20GS, a highly sensitive proton precession gradiometer with two aligned sensors, which has an RMS resolution of 0.05 pico-Tesla (pT). In a further embodiment, the condition meter 118 includes the Ecoseal MAG-01H, single-axis fluxgate magnetometer with a resolution of 0.1 nT. In one embodiment, the condition meter 118 is electrically connected to the driver 126 via the condition meter cable 128. In some embodiments, the condition meter 118 may be connected via any of a variety of communication means known in the art—wired and/or wireless. In one embodiment, the use of the condition meter 118 allows the driver 126 to sense the ambient magnetic environment and adapt its output to account for this field.

In addition to being limited by the output device, the frequency range of the current embodiment may be limited by a compensation network. In one embodiment, the compensation network may be a resistor and capacitor network that is matched to the impedance of the output device 110. In certain embodiments, the compensation network may be used to negate the reactance of the coil over a small range of frequencies, for example, from 0.1 Hz to 500 Hz. In other embodiments, the compensation network may negate the reactance of the coil over a smaller or larger range of frequencies. In one embodiment, the system 100 and the output device 110 are wired in parallel with the compensation network, to thereby provide a standardized impedance, with minimum variation between individuals in production lots. As a result of such impedance matching, alternative sets of the output device 110 may be used in the system 100 without the need for recalibration.

In one embodiment, the communication cable 122 is a wired electrical connection between the processor 114 and the driver 126. The communication cable 122 may provide a standard digital serial communication means (e.g., Ethernet, RS-232, USB) to enable the communication of operational and other commands, and to exchange other data, between the processor 114 and the driver 126. In addition, in some embodiments, the communication cable 122 may provide power and ground to the driver 126, e.g., utilizing a POE-Ethernet cable.

In various embodiments, such as those in which the output device 110 comprises one or more magnetic coils, the need may exist for the driver 126 to be capable of being located near the output device. In one embodiment, such a configuration minimizes cable length to the coils, which can be a source of electrical noise and therefore increased error. Various embodiments of the present invention meet this need. In one embodiment, the use of the communication cable 122 allows the driver 126 to be located near the output device 110. One advantage of such an embodiment may be minimizing the cable length of the driver cable 124, and in so doing, significantly lowering electrical noise and error.

In one embodiment, the driver cable 124 may be short electrical cables with connectors that provide an analog signal that powers the output device 110. In some embodiments, such as those in which the output device comprises a coil assembly, the driver cable 124 comprises one or more coil cables. The coil cables may provide power to one or more coils, such as magnetic coils. In one embodiment, the output device 110 is a coil assembly that produces the specific magnetic waveform (amplitude and frequency) required for magnetic therapy. For example, in one embodiment, the driver cable 124 may comprise coil cables that are a shielded twisted pair with a 156 Molex connector. In one embodiment, the driver cable 124 comprises coil cables wired between the output device 110 and the driver 126.

In one embodiment, the driver 126 may be a low-level electronic waveform generator, for use in the system 100. Also, in one embodiment, the processor 114 may transmit signals comprising operational commands, such as normal operation on/off, AC calibration, and DC calibration to the driver 126. The processor may transmit the signals via the communication cable 122, and/or any other communication means known in the art—wired and/or wireless. For normal operation, the processor 114 may transmit signals comprising specific magnetic waveform parameters, such as waveform type (e.g., sinusoidal, square, sawtooth), amplitude (e.g., 0.032 micro-gauss, 0.017 micro-gauss, 0.075 micro-gauss) and frequency (e.g., 0.3 Hz, 0.8 Hz, 5 Hz, 10 Hz) to the driver 126. Subsequently, the driver 126 may perform normal operation as described in detail in the discussion of FIGS. 4 and 5 and methods 400 and 500, or AC calibration as described in method 600, or DC calibration as described in method 700.

In a further embodiment, the driver 126 possesses shielding elements that prevent electromagnetic radiation emanating from the driver 126 from interfering with the operation of the system 100, for example, a chassis exterior having 20-thousands (0.02") steel, or 10-thousands (0.01") mu metal. In other embodiments the driver may comprise shielding made from stainless steel, aluminum, or some other metal known in the art.

In one embodiment, the condition meter cable 128 may be a wired electrical connection between the condition meter 118 (such as a magnetometer) and the driver 126. The condition meter cable 128 may provide a standard digital serial communication means, for example, universal serial bus (USB), recommended standard 232 (RS-232) or serial peripheral interface bus (SPI), to enable the communication of magnetic field data from the condition meter 118 to the driver 126. In a further embodiment, the condition meter cable 128 may provide power and ground to the condition meter 118.

Figure 2:
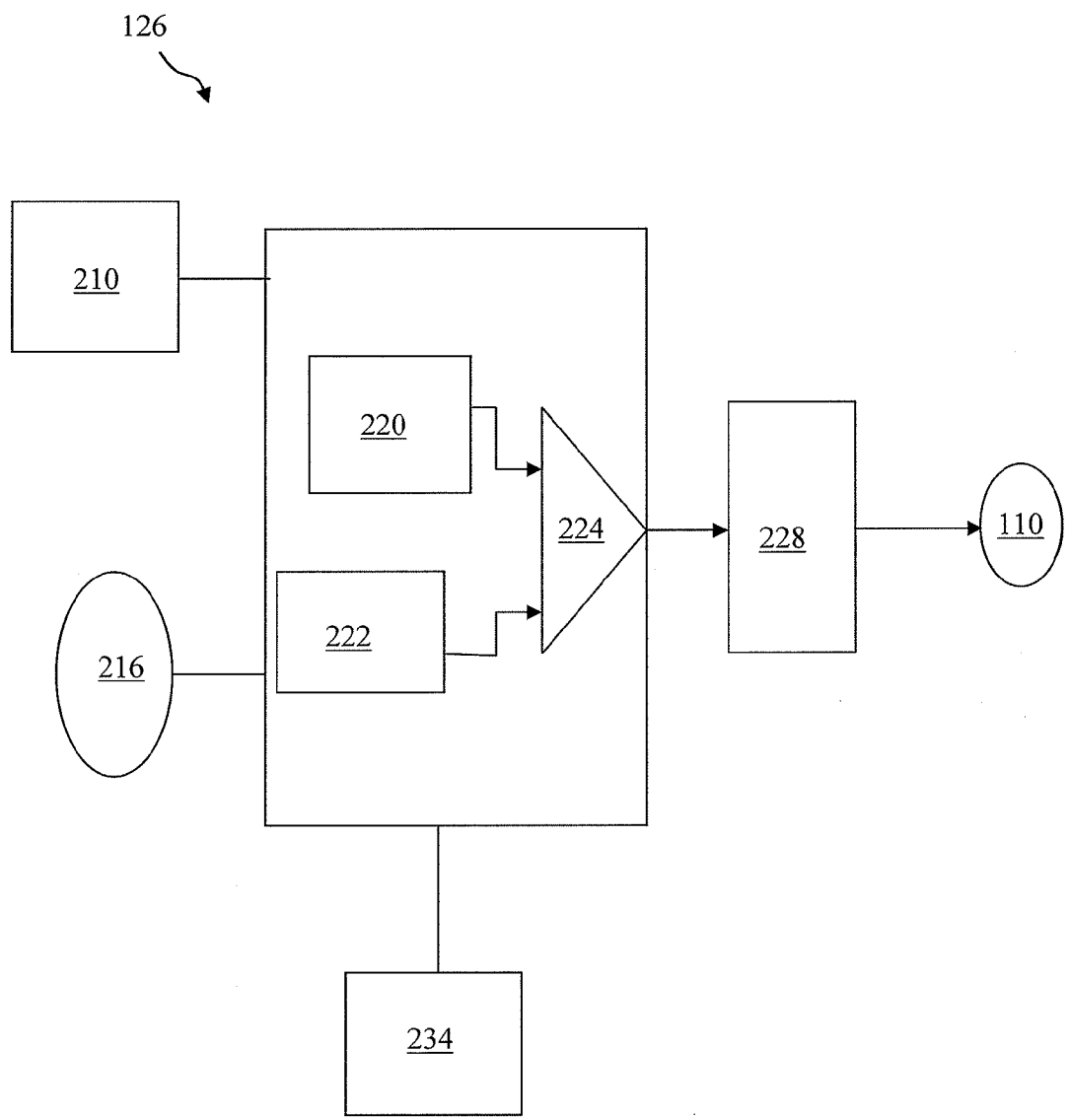
FIG. 2 is a functional block diagram illustrating a driver according to one embodiment of the present invention.

The present invention relates to a programmable, low-noise, precise and accurate driver. FIG. 2 is a functional block diagram illustrating a driver according to one embodiment of the present invention. In some embodiments, the driver 126 may provide a signal. In a further embodiment, the driver 126 may provide a signal to the output device 110, which may provide a magnetic field. In further embodiments, the driver 126 may provide a signal to an output device 110 which may provide an accurate and precise magnetic field which, for example, may be useful for providing magnetic therapy.

In one embodiment, the driver 126 comprises a DAC-1 220, a DAC-2 222, and a differential amplifier 224. In a further embodiment, the driver comprises an attenuator 228. In a further embodiment, the driver comprises a voltage reference source (VREF) 216. In a further embodiment, the driver comprises a wave generator, such as a signal generator 210.

In one embodiment, the driver 126 comprises a first and second digital to analog conversion devices (DAC-1 220 and DAC-2 222). As described herein, the DAC-1 220 and DAC-2 222 may be used to increase accuracy and precision while reducing errors. In other embodiments, the driver 126 comprises more than two digital to analog conversion devices. For example, in some embodiments, driver 126 comprises three or more digital to analog converters. In such an embodiment, the three or more digital to analog conversion devices may be used to increase accuracy and precision, while reducing errors.

In a further embodiment, the driver 126 may comprise only one digital to analog converter. In one embodiment, the driver 126 may comprise a filter between the signal generator 210 and the digital to analog conversion device. The filter may be a low-pass filter which may attenuate the signal produced by the signal generator 210. In such an embodiment the filter may be, for example, an active or a passive low-pass filter. In one embodiment, a single ended to differential conversion device resides between the digital to analog conversion device and the differential amplifier 224. Also, the driver 126 may comprise a DC offset servo device in communication with the single ended to differential conversion device. The DC offset servo device may use error-sensing feedback to correct the performance of the single ended to differential conversion device. Further, the single ended to differential conversion device may provide two outputs to differential amplifier 224. In one embodiment, the remainder of the driver (after the differential amplifier 224) is identical to a two-DAC system. In such a single-DAC embodiment, a precision reference is required and any resulting errors at the system output may be directly related to the reference.

In one embodiment, the DAC-1 220 and DAC-2 222 provide analog outputs to different inputs of the differential amplifier 224. Thus, in one embodiment, the differential amplifier 224 is a differential amplifier housed in the driver 126. In one embodiment, the differential amplifier 224 receives input from the DAC-1 220 and DAC-2 222. In a further embodiment, the differential amplifier 224 provides output to the attenuator 228. In some embodiments, DAC-1 220, DAC-2 222, and differential amplifier 224 work together to assist in increasing precision while reducing errors by, for example, producing corrected analog signals using the correction factors computed in the methods depicted in FIGS. 6 and 7, and described in methods 600 and 700.

In one embodiment, the driver 126 may comprise an attenuator 228. In one embodiment, the attenuator 228 may receive input from the differential amplifier 224. Devices suitable for use in attenuator 228 include metal film resistor networks having an accuracy of up to 0.1%. The attenuator 228 may be housed in the driver 126. In one embodiment, the attenuator 228 is capable of dividing down analog signals to create low-level analog signals. For example, in one embodiment, the attenuator 228 is capable of producing an attenuation of 1:1, or unity, to an attenuation of $1:1 \times 10^{-15}$. In a further embodiment, the attenuator 228 is a programmable attenuator, which can be set to various attenuation levels. The use of a manual attenuator may be problematic in that manual attenuators may be too imprecise and inaccurate for use in low-level magnetic therapy drivers, resulting in magnetic fields that deviate significantly from the desired output. In addition, for normal operation, manual calibration of the attenuator is generally required for each coil. Consequently, whenever a coil is changed to alter a magnetic therapy treatment, recalibration is necessary. This approach can be prone to operator error. As a result, a need exists for a magnetic therapy driver that can be used with alternative sets of coils without the need for recalibration.

Also, manual attenuators can be problematic in that the discrete resistors used by manual attenuators may result in significant electrical noise (e.g., 1/f noise, and shot noise). As a result, a resistive attenuator may introduce error into the field delivered by the driver. Thus, a low-noise driver is needed. Furthermore, the ability to create sequential and programmable time-sequences of different waveforms (e.g., sinusoidal or square) is also essential for many magnetic therapy applications. In earlier solutions, complex regimes of time sequenced magnetic waveforms were accomplished by manual switching of the signal generator and manual attenuator. This approach can be inaccurate, cumbersome and prone to operator error. Consequently, a precise control of electronic signal waveforms that drive the magnetic coils is required. As a result, a programmable driver, including a programmable attenuator is needed. Embodiments of the present invention meet these needs.

In one embodiment, the driver 126 may include a voltage reference source (VREF 216). The VREF 216 may be used in the driver 126 to provide a highly accurate and low temperature drift voltage reference. As explained herein, there is a need to increase accuracy and precision while reducing errors. The VREF 216 assists in meeting these needs. The accuracy of the system can be quantified by how well the VREF 216 matches a known standard (repeatability) as well as how much the VREF 216 changes over time (stability). The VREF 216 may be connected to one or more of the various devices via any communication means known in the art including, for example, a system bus.

In one embodiment, the driver comprises a signal generator 210. In one embodiment, the signal generator 210 may be a digitally programmable on-board low noise—low frequency sinusoidal signal generator. The digital control input of the signal generator 210 may be electrically connected to the microcontroller 234 via known methods. The signal generator 210 may also receive a voltage reference input from the VREF 216.

In some embodiments, the driver may comprise a microcontroller 234. The microcontroller 234 may be an on-board digitally programmable micro-controller device, such as a microprocessor with programmable memory, or other microcontroller devices known in the art. In some embodiments, the microcontroller 234 communicates with the processor 114. This communication may comprise transmitting signals via the communications cable 122, or other communications means known in the art, such as wireless communications devices. In certain embodiments, the microcontroller 234 may communicate with the magnetometer 118. This communication may comprise transmitting signals via the magnetometer cable 128, or other communications means known in the art, such as wireless communications devices.

Figure 3:
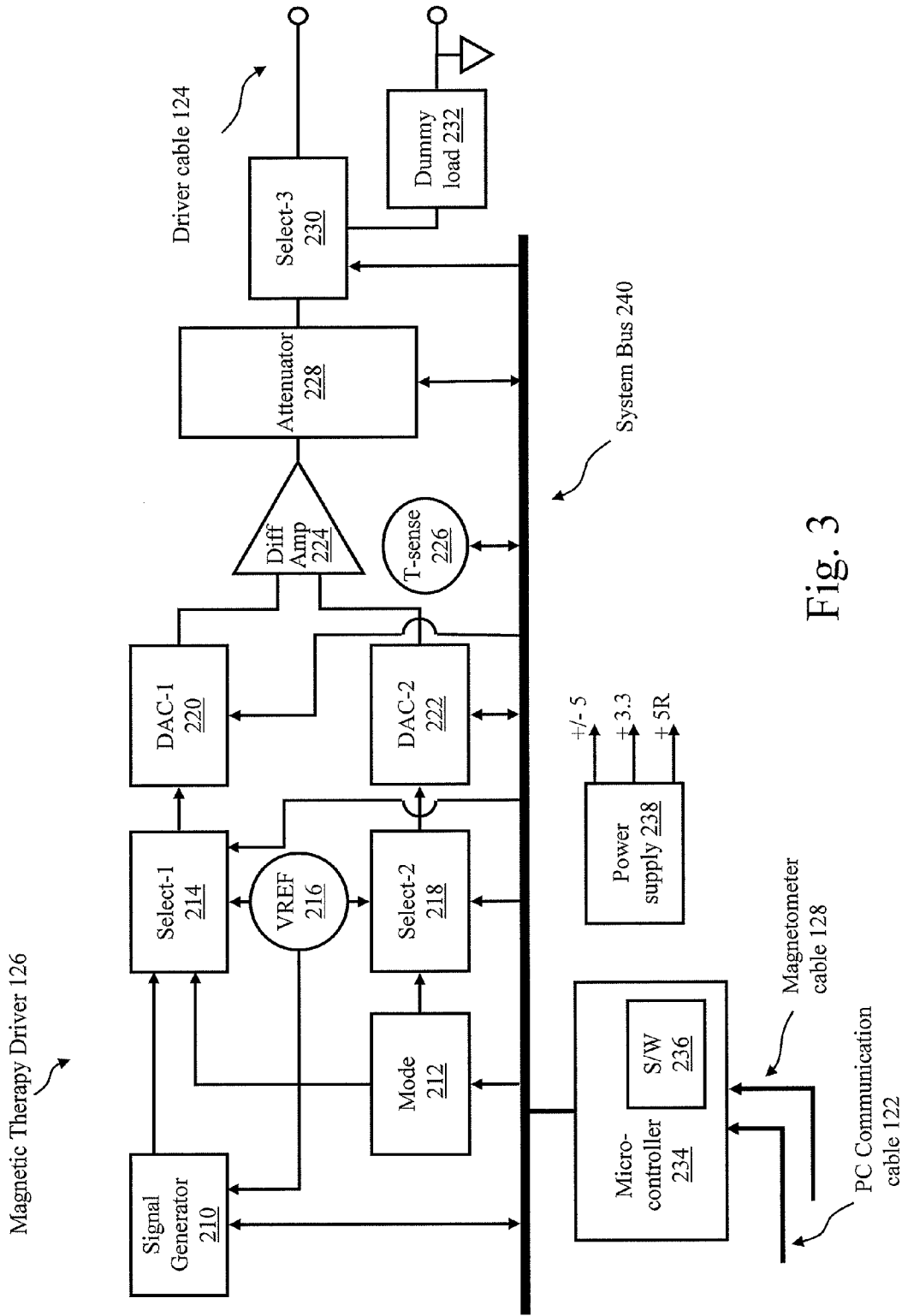
FIG. 3 is a functional block diagram illustrating a driver according to one embodiment of the present invention.

FIG. 3 is a functional block diagram illustrating a driver 126 for use according to one embodiment of the present invention. In one embodiment, the driver 126 provides a programmable, low-noise, precise and accurate driver for use in the system 100.

As illustrated in FIG. 3, the driver 126 may include a first digital to analog converter component (DAC-1) 220, a second digital to analog converter component (DAC-2) 222, and a differential amplification component, such as a differential amplifier (Dif Amp 224). In a further embodiment, the driver 126 may also include an attenuator 228. In a further embodiment, the driver 126 may also include a voltage reference source (VREF) 216. In a further embodiment, the driver 126 may also include a signal generator 210. In a further embodiment, the driver 126 may also include one or more relay devices. In some embodiments, the driver includes the following relay devices: a mode 212, a select-1 214, a select-2 218, and a select-3 230. In a further embodiment, the driver 126 may also include a microcontroller 234. In some embodiments, the microcontroller 234 may also include software (S/W) 236. In some embodiments, the driver 126 may also include a temperature sensing device (T-sense) 226. In some embodiments, the driver 126 may also include a dummy load 232. In some embodiments, the driver 126 may also include a power supply 238. In some embodiments, the communications cable 122, condition meter cable 128, and driver cable 124 communicatively connect the elements represented in FIG. 1 to the elements represented in FIG. 3.

In one embodiment, the driver comprises a signal generator 210; a first relay device (select-1 214) connected to receive output from the signal generator 210; a first digital to analog converter (DAC-1 220) connected to receive output from the first relay device (select-1 214); a voltage reference source (VREF 216); a second relay device (select-2 218) connected to receive output from the voltage reference source (VREF 216); a second digital to analog converter (DAC-2 222) connected to receive output from the second relay device (select-2 218); an amplifier (differential amplifier 224) connected to receive input from the first and second digital to analog converters (DAC-1 220 and DAC-2 222); a programmable attenuator 228 connected to receive input from the amplifier (differential amplifier 224); a mode device 212 connected to provide input to the first and second relay devices (select-1 214 and select-2 218); a bus 240 connected to the signal generator 210, first and second relay devices (select-1 214 and select-2 218), first and second digital to analog converters (DAC-1 220 and DAC-2 222), attenuator 228, and mode device 212; and a controller 234 connected to the bus 240.

Thus, as illustrated above in FIG. 2 and in FIG. 3, in one embodiment the driver comprises a signal generator 210. In one embodiment, the signal generator 210 may be a digitally programmable on-board low noise—low frequency sinusoidal signal generator. An example signal generator 210 is Analog Device part number: AD9832, which provides 0-500 Hz operation at a resolution 1 micro-hertz, with −60 dB noise rejection, and is programmable over a Serial Peripheral Interface (SPI) bus. The digital control input of the signal generator 210 may be communicatively connected to the microcontroller 234. In one embodiment, the connection may be through a system bus 240; or other types of connections known in the art may be used. The signal generator 210 may also receive a voltage reference input from the VREF 216. In one embodiment, the voltage reference input may be 1.024 volts, in other embodiments the voltage reference may be a different voltage. In one embodiment, the sinusoidal output of the signal generator 210 is electrically connected to the select-1 214.

In one embodiment, the driver 126 comprises one or more relay devices to relay signals from one component to another. The relay devices may include latching relay devices. Examples of suitable latching relay devices include low-loss/long-life signal relays, with low closed impedance and high open impedance (e.g., gold-contacts), which can be latched without the continuous application of power. In other embodiments, the relay devices may comprise solid state relays.

Such relay devices may be used to switch analog signals such as sinusoidal signals, or digital control signals. Embodiments of latching relay devices are shown as the Mode 212, select-1 214, select-2 218, and select-3 230 in FIG. 3. For example, the mode 212 may receive digital control signals from the microcontroller 234 over the system bus 240 and may further provide digital control output signals to the relay devices, select-1 214 and select 2-218. The select-1 214 and select-2 218 may receive digital control signals directly from the mode 212, or may receive other digital signals from the microcontroller 234. In one embodiment, such signals are received over the system bus 240. In addition, the relay devices may be used to relay signals from the signal generator 210, and a voltage reference signal from the VREF 216 to the DAC-1 and DAC-2. In one embodiment, the output signals of the select-1 214 and select-2 218 are electrically connected to the DAC-1 220 and DAC-2 222 respectively. Also, the select-3 214 may receive digital control signals from the microcontroller 234. In one embodiment these digital control signals are received over the system bus 240. Also, the select-3 214 may receive an analog signal input from the attenuator 228. The outputs of the select-3 214 may be electrically connected to the coil cables 124. Also, the signals from the select-3 214 may be connected to a dummy load 232, which is a device used to simulate an electrical load.

In one embodiment, the driver 126 may include a voltage reference source (VREF 216). As noted herein, the voltage reference source (VREF 216) may be used in the driver 126 to provide a highly accurate and low temperature drift voltage reference. In certain embodiments, the accuracy of the system is quantified by how well the voltage reference source (VREF 216) matches a known standard (repeatability), and/or how much the voltage reference source (VREF 216) changes over time (stability). An example of a suitable voltage reference source is National Semiconductor part number: LM4140 which provides 1.024 volts at ±0.1% accuracy with a 3-5 ppm/°C. temperature coefficient. In one embodiment, the VREF 216 is directly connected to the signal generator 210, select-1 214 and select-2 218.

The driver 126 may comprise at least a first and second digital to analog conversion device (DAC-1 220 and DAC-2 222). The DAC-1 220 and DAC-2 222 may be used to increase accuracy and precision while reducing errors. An example of a suitable digital-to-analog conversion device is the Analog Devices digital-to-analog converter, part number AD5680 which provides an 18-bit DAC, with 2 LSB accuracy, less than 1 LSB linearity, 16-bit resolution, and a 300 Hz update rate. In other embodiments, a different digital to analog converter may be used. The DAC-1 220 and DAC-2 222 may, in certain embodiments, receive analog inputs from the select-1 214 and select-2 218 respectively. In further embodiments, the DAC-1 220 and DAC-2 222 may receive digital inputs from the system bus 240. The digital inputs provided by the system bus may include electrical signals from the microcontroller 234.

In one embodiment, the DAC-1 220 and DAC-2 222 provide analog outputs to different inputs of the differential amplifier 224. Thus, in one embodiment, the differential amplifier 224 is a differential amplifier housed in the driver 126. An example of a suitable device for use as a differential amplifier 224 is Linear Technology part number: LT1920 which provides −100 dB noise rejection, 1 millivolt offset, and −85 dB CMRR (to a few KHz). In one embodiment, the differential amplifier 224 receives input from the DAC-1 220 and DAC-2 222. In a further embodiment, the differential amplifier 224 provides output to the attenuator 228. As explained herein, there is a need to increase accuracy and precision while reducing errors. In some embodiments, the DAC-1 220, DAC-2 222, and differential amplifier 224 work together to assist in meeting this need by, for example, producing corrected analog signals using the correction factors computed in the methods depicted in FIGS. 6 and 7.

In one embodiment, the driver may comprise a temperature sensor 226. For example, as shown in FIG. 3, the temperature sensor 226 may be located in a region of thermal conductivity with the output device 110. In one embodiment, the output device 110 comprises a coil assembly, and the temperature sensor 226 is located within the coil housing. In this way, the driver may be capable of adjusting its output in proportion to ambient temperature, such that changes in temperature will have a reduced effect on the precision and accuracy of the magnetic therapy. The temperature sensor 226 may be located within the driver 126. An example of a suitable device for the temperature sensor 226 is Microchip part number TC77-5.0MC, which provides a ±1° C. accuracy and 13 bit resolution. The temperature sensor 226 may provide a digital output to output to the microcontroller 234 via the system bus 240. In some embodiments, the use of the temperature sensor 226 allows the driver 126 to adjust its output in response to temperature changes of, for example, the output device 110.

In one embodiment, the driver 126 may comprise an attenuator 228. As noted in the description for FIG. 2, the attenuator 228 may be housed in the driver 126. A number of types and features of attenuators are known in the art. For example, attenuation may be provided by passing the signal through voltage divider circuits comprising resistors. Alternatively, a transformer with a suitable turns ratio may provide attenuation of either voltage or current. In such an embodiment, one would measure the resultant value to determine the result. Further, in such an embodiment the attenuated signal in this method is not exactly a function of the turns ratio. A reason for this may be the existence of variations in transformer efficiency. One way of providing an adjustable means of attenuation may include optically coupling the signal to a receiver. However, in such an embodiment the optical coupling coefficient may vary as a function of the signal levels. Also, the noise levels can be quite low using alternate methods, but the noise spectra is non-Gaussian, and therefore may be more difficult to filter.

In one embodiment, the attenuator 228 is capable of dividing down analog signals to create low-level analog signals. For example, in one embodiment, the attenuator 228 is capable of producing an attenuation of 1:1, or unity, to an attenuation of $1:1 \times 10^{-15}$. In a further embodiment, the attenuator 228 is a programmable attenuator. Programmable attenuators can be set and/or preset to various attenuation levels, thereby avoiding the problems seen with manual attenuators.

In one embodiment, the attenuator 228 may receive input from the differential amplifier 224. In certain embodiments, the attenuator receives such input via the system bus 224. In some embodiments, the attenuator 228 may provide an output to the select-3 230. Devices suitable for use in attenuator 228 include metal film resistor networks having an accuracy of up to 0.1%.

As shown in FIG. 3, the driver 126 may comprise a dummy load 232. In some embodiments, the dummy load 232 may be a resistive load housed within the driver 126 that provides an output impedance alternative to the load provided by output device 110. The dummy load 232 is capable of simulating an electrical load. For example, in some embodiments, such as when used with AC and DC calibration (e.g., methods depicted in FIGS. 6 and 7, respectively), the dummy load receives an electrical load, which is then measured. In some embodiments, the dummy load 232 receives input from the select-3 230. In one embodiment, a 1KΩ resistor is suitable for the dummy load 232.

In some embodiments, the driver may comprise a microcontroller 234. The microcontroller 234 may be an on-board digitally programmable micro-controller device, such as microprocessor with programmable memory, or other microcontroller devices known in the art. An example of a suitable microcontroller for use as microcontroller 234 is the Atmel AT32UC3A0512 which has the following characteristics: 32-bit operation, a flash ROM, Ethernet, an I²C port, and an SPI port. Further, the Atmel AT32UC3A0512 development system includes software to operate many functions of the microcontroller. Further benefits of the Atmel AT32UC3A0512 include relatively low cost, upgradability of functions, and availability of peripherals.

In some embodiments, the microcontroller 234 communicates with the processor 114. This communication may take place via the communications cable 122, or other wired or wireless communications means known in the art.

In certain embodiments, the microcontroller 234 may communicate with the condition meter 118. This communication may take place via the condition meter cable 128, or other communications means known in the art, such as wireless communications devices.

The microcontroller 234 may, in certain embodiments, communicate within the driver 126 over the system bus 240 (e.g., via its I$^2$C and/or SPI ports) with the signal generator 210, and/or the mode 212, and/or the select-1 214, and/or the select-2 218, and/or the select-3 230, and/or the DAC-1 220, and/or the DAC-2 222, and/or the T-sense 226, and and/or the attenuator 228. In some embodiments, the software (S/W 236), which resides within the non-volatile memory of the microcontroller 234 (e.g., flash ROM, NVRAM), is the firmware that assists in enabling the functionality of the driver 126, thereby providing a programmable driver.

In some embodiments, the driver 126 may comprise a power supply 238. The power supply 238 may comprise any standard DC/DC power supply. For example, in some embodiments, the power supply has ±5 volt and +3.3 volt outputs and a wide range of DC input voltages. In one embodiment, the power supply has very low radiated and conducted noise. The power supply may achieve low noise by using specific fixed frequency converters. These converters may allow more precise filtering of noise components. Further, the use of smaller targeted power supplies may generate less total noise. The power supply 238 may receive input power via the communications cable 122. Also, the power supply 238 may supply electrical output power to the driver 126. Example devices which are suitable for the power supply 238 are standard switch-mode or linear DC supplies. In other embodiments, other power supplies known in the art may be used.

In one embodiment, the driver 126 comprises a system bus 240. The system bus 240 may be a digital communication bus. In some embodiments, the microcontroller 234 uses the system bus 240 to communicate to and from other digital components within the driver 126. In various embodiments, the system bus 240 may comprise one or more of any digital communication means that can interconnect the driver 126. For example, the system bus 240 may comprise a 32-bit parallel bus, and/or a SPI serial bus, and/or I$^2$C serial bus, among others.

FIG. 3 shows one possible configuration of driver 126 and its associated components. Other configurations of driver 126 and associated components are possible. For example, in one embodiment, the output device 110 comprises a coil assembly, which may be driven single-endedly through the select-3 230 as shown in FIG. 3, in which case the current is returned to ground. In a further embodiment, in which the output device 110 comprises a coil assembly, the two terminals of the coil assembly may be driven differentially through two switches within the driver 126. In such an embodiment, the coil assembly would be in DC isolation from ground, thereby reducing the effect of spurious signals on driver 126. In addition, the current and/or voltage waveform of the coil assembly may be fed back to the driver 126 and reprocessed using servo techniques. Such a technique may have benefits, including minimizing voltage offset errors within the driver 126.

In some embodiments a method of operating a magnetic field generating device according to one embodiment of the present invention may comprise receiving at least one calibration factor. In some embodiments, a method of operating a magnetic field generating device may comprise receiving signals from a first digital to analog converter and a second digital to analog converter. In some embodiments, a method of operating a magnetic field generating device may further comprise using the signals and the at least one calibration factor to calibrate the driver.

In some embodiments of a method of operating a magnetic field generating device, the at least one calibration factor is both an AC calibration factor and a DC calibration factor. In some embodiments of a method of operating a magnetic field generating device the at least one calibration factor is an AC calibration factor. In some embodiments of a method of operating a magnetic field generating device the at least one calibration factor is a DC calibration factor.

In some embodiments of a the present invention, the AC calibration factor is determined by a method comprising: receiving an AC calibration level; directing the driver to produce an output signal; measuring the output signal; and determining the accuracy of the output signal.

In some embodiments of a the present invention, the DC calibration factor is determined by a method comprising: receiving a DC calibration level; directing the driver to produce an output signal; measuring the output signal; and determining and storing a DC offset, based at least in part on the measurement of the output signal.

Figure 4:
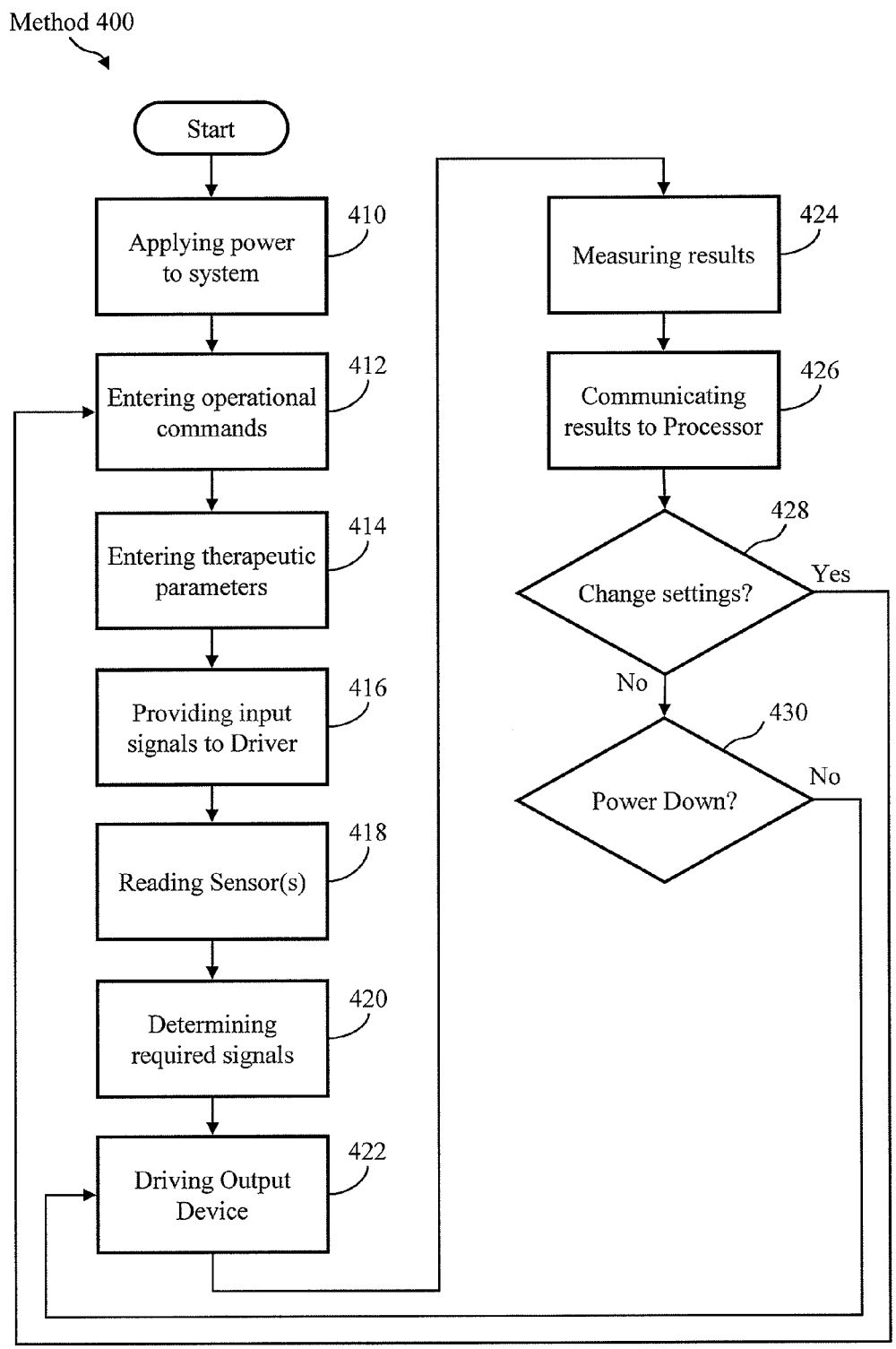
FIG. 4 is a flow diagram illustrating a method of operating the driver according to one embodiment of the present invention.

FIG. 4 is a flow diagram illustrating an embodiment of a method 400 of operating a driver 100 of the present invention. The method 400 includes the process for initialization and normal operation of the driver 126 according to one embodiment of the present invention. FIGS. 1, 2, and 3 are referenced throughout the steps of the method 400. In one embodiment, the method 400 comprises the following steps:

Step 410: Applying Power to the System:

In one embodiment, power is applied to the processor 114. Also, power may be supplied to the condition meter 118. Also, power may be supplied to the driver 126. Also, power may be supplied to the sensors. In one embodiment, the power supply 238 within the driver 126 supplies power to all circuits within the driver 126. In a further embodiment, the power supply 238 provides ±5 v, +3.3 v of power. Next, the method 400 may proceed to step 412.

Step 412: Entering Operational Commands:

In one embodiment, commands are provided to the system. These commands may include instructions regarding the operation of the system. In some embodiments, an operator enters the commands using the processor 114. In a further embodiment, the operator enters the commands via a user interface communicatively connected to the processor 114. According to various embodiments, examples of system operation commands may include those that implement a desired therapeutic regime and those that perform calibration of the driver 126. Calibration of the driver may be accomplished by performing an AC or DC calibration. In some embodiments, the AC or DC calibration may determine the AC or DC calibration factors. Illustrative embodiments of AC and DC calibration are described in the discussion of methods 600 and 700. Next, the method 400 may proceed to step 414.

Step 414: Entering Therapeutic Parameters:

In one embodiment, therapeutic parameters are provided. In some embodiments, the therapeutic parameters are provided using the processor 114. In a further embodiment, the therapeutic parameters are provided via the user interface of the processor 114. In various embodiments, the parameters are provided in a variety of ways, for example, by condition to be treated, by a regime code, or by waveform parameters, such as magnetic waveform type, amplitude and frequency (i.e., sinusoidal, 0.1 nano-Tesla, 10 Hz). In a further embodiment, the therapeutic parameters are provided by software without the need for manual entry by an operator. For example, the processor 114 may receive data containing operational commands for the desired therapeutic regime from a centralized server via a network connection. Next, the method 400 may proceed to step 416.

Step 416: Providing Input Signals to Driver:

In one embodiment, input signals are provided to the driver. In such an embodiment, the input signals may comprise a command for the system to operate in normal operation mode. In some embodiments, processor 114 provides the input signals. In some embodiments, the input signals may be transmitted via the communications cable 122. Next, the method 400 may proceed to step 418.

Step 418: Reading Condition Meter and Other Sensors:

In one embodiment, the condition meter 118 is a magnetometer that measures the ambient magnetic field between the coils of the output device 110, which may comprise a coil assembly. In a further embodiment, the magnetometer communicates digital ambient magnetic field data to the microcontroller 234. In one embodiment, this communication may take place via the condition meter cable 128. In other embodiments, this communication may take place via other communication means known in the art, such as wireless communications. In one embodiment, the T-sense 226 may sense the temperature of the output device 110. Also, the T-sense 226 may communicate digital temperature data to the microcontroller 234. In some embodiments, this communication takes place via the system bus 240.

In some embodiments, other sensors provide sensor signal comprising data for controlling the driver. In various embodiments the sensors may measure a variety of biometric and/or physical data (e.g., humidity, pressure, heart rate, blood pressure, EKG, EEG). In some embodiments, the sensors provide the sensor signals to a communication means. The communication means may comprise either wired (e.g., USB, IEEE 1394) or wireless (802.11, Bluetooth). In some embodiments, the sensors provide sensor signals to the microcontroller 234, under control of the S/W 236. In further embodiments, the sensors provide sensor signals to the processor 114. The sensor signals comprise data which may comprise ambient magnetic field data, and/or the temperature data, and/or the sensor data. The sensor may transmit signals via the communication cable 122. In some embodiments, the ambient magnetic field data, and/or temperature data, and/or the sensor signals are communicated to a centralized server. This communication may be done via a network of any type known in the art, including wired and wireless networks. Next, the method 400 may proceed to step 420.

Step 420: Determining Required Signals:

In one embodiment, the processor 114 determines the required signals. In some embodiments, the processor 114 uses the calculations to compensate for one or more conditions. In such an embodiment, the conditions may comprise ambient magnetic conditions, temperature, and/or other external conditions. In some embodiments, T-sense 226 and/or the condition meter 118 detect the external conditions. The processor 114 may determine one or more compensated waveform correction factors required to produce a therapeutic dose of magnetic field. As explained herein, using the correction factors assists in meeting the currently felt need for providing accurate and precise low-level magnetic fields while reducing errors. The processor 114 may determine an electronic waveform to produce a therapeutic dose of magnetic field. Additionally or alternatively, the processor 114 may determine a correction factor to apply to the waveform to compensate for the ambient magnetic field and the temperature of the output device 110.

In some embodiments, the processor 114 makes this determination using techniques such as calculating the inverse polarity of the ambient magnetic field. For example, the system may use a magnetometer to measure the total magnetic field within the coils. Then the processor 114 may determine a compensation value by comparing the measured field to the expected field. Then, the compensation value may be generated and applied to the drive signal. Further, the processor 114 may determine compensation for the temperature of the coil assembly, and based on this determination apply additional, or reduced, electric current to the coil assembly.

For example, in one embodiment, the processor 114 may determine temperature compensation to apply to the drive signal using an algorithm obtained using a general set of coils. In such an embodiment, the temperature coefficient of copper and the elongation of the windings will change the actual magnetic field for a given current. The processor may use this known relationship, and the measured temperature of the windings to determine an adjustment to the final scale factor. In one embodiment, for example, an equation that may be used to calculate the final scale factor is (old value*(1+[normalized temperature]*[sensitivity factor])). The sensitivity factor may be determined experimentally. Also, correction factors based on AC and/or DC correction factors may be used.

In some embodiments, processor 114 performs one or more of these steps. For example, in some embodiments, processor 114 may comprise a memory which stores AC and DC correction factors. Also, the processor 114 may determine the electronic waveform. Next, the method 400 may proceed to step 422.

Step 422: Driving Output Device:

In one embodiment, the output device 110, such as a coil assembly, produces a magnetic field. In some embodiments, the driver 126, energizes the coils of the coil assembly to produce the magnetic field. The magnetic field may comprise the therapeutic dose of magnetic field computed in step 420. This process is explained in more detail in FIG. 5 and the accompanying description. Next, the method 400 may proceed to step 424.

Step 424: Measuring Results:

In one embodiment, the magnetic field is measured. In some embodiments, the condition meter 118 comprises a magnetometer that measures the magnetic field within the output device 110, such as a coil assembly. The magnetic field may be a combination of the pre-existing ambient field and the field that the system 100 generates. In some embodiments, the magnetometer may transmit a signal comprising the measurement results the microcontroller 234. The magnetometer may transmit the signal via the condition meter cable 128. In one embodiment, the T-sense 226 and/or other sensors that measure a variety of physical and biometric data transmit signal via a communication means. In various embodiments, the communication means may be any communication means known in the art, either wired or wireless. Further, in some embodiments, at least a portion of the data may be communicated to the microcontroller 234, under control of the S/W 236. Next, the method 400 may proceed to step 426.

Step 426: Communicating Results to Processor:

In one embodiment, the results are communicated. For example, in some embodiments the microcontroller 234, under control of the S/W 236, communicates the results. The results may include magnetic field and other sensor inputs measured in step 424. In some embodiments, the results are communicated to the processor 114. The communication may take place via the communication cable 122. In other embodiments, the communication may take place via any communication means known in the art—wired and/or wireless.

After receiving the data, in some embodiments, the processor 114 displays and/or analyzes at least some of the data. In various embodiments, the data displayed and/or analyzed relates to the operational status of the magnetic therapy system 100 and data from the sensors. Examples of such data may include the resultant magnetic field parameters, and/or whether the operation is within proper limits of operation, and/or if a variety of biometric data are sufficiently positive to proceed with the therapeutic regime. In one embodiment, while in continuous operation, the processor 114 displays various operational and sensor data. In some embodiments, processor 114 may be communicatively connected to a display. In such an embodiment, for example, the display may comprise an LCD display, an LED display, or a CRT display. In some embodiments, the processor 114 may use the display to display various operational and sensor data. This data may include the resultant therapeutic magnetic field parameters, and/or a variety of physical and/or biometric sensor data from the sensors. This sensor data may represent a variety of physical parameters including the physiological states of recipients of magnetic therapy, for example, an abnormally high pulse rate. Next, the method 400 may proceed to step 428.

Step 428: Change Settings?:

In one embodiment, the choice to change settings is presented. In some embodiments, the processor 114 prompts the operator to determine whether changes to the operational or therapeutic parameters are necessary. This prompt may be based on the results of step 426. In one embodiment, if directed to change settings, the processor 114 uses an algorithm to recalculate and communicate new electrical waveform parameters to the driver 126. Further, in some embodiments, the new electrical waveform parameters may be used to alter the output of the magnetic therapy system 100. If the decision is made to change the settings, then the method 400 proceeds to step 430. If the decision is made not to change the settings, then the method 400 may proceed back to step 412.

Step 430: Power Down?:

In one embodiment, the decision is made whether to power down the system 100. In some embodiments, the operator determines whether to power down the system 100. In other embodiments, the processor 114 determines whether to power down the system 100. If the decision is made to power down, then the method 400 ends. If the decision is made not to power down, then the method 400 may return to step 422.

As explained above, an aspect of providing a magnetic field according to one embodiment of the invention is driving the output device 110. As further explained above, in one embodiment the output device 110 comprises a coil assembly. This process is represented by step 422 in FIG. 4, and is explained in more detail below.

Figure 5:
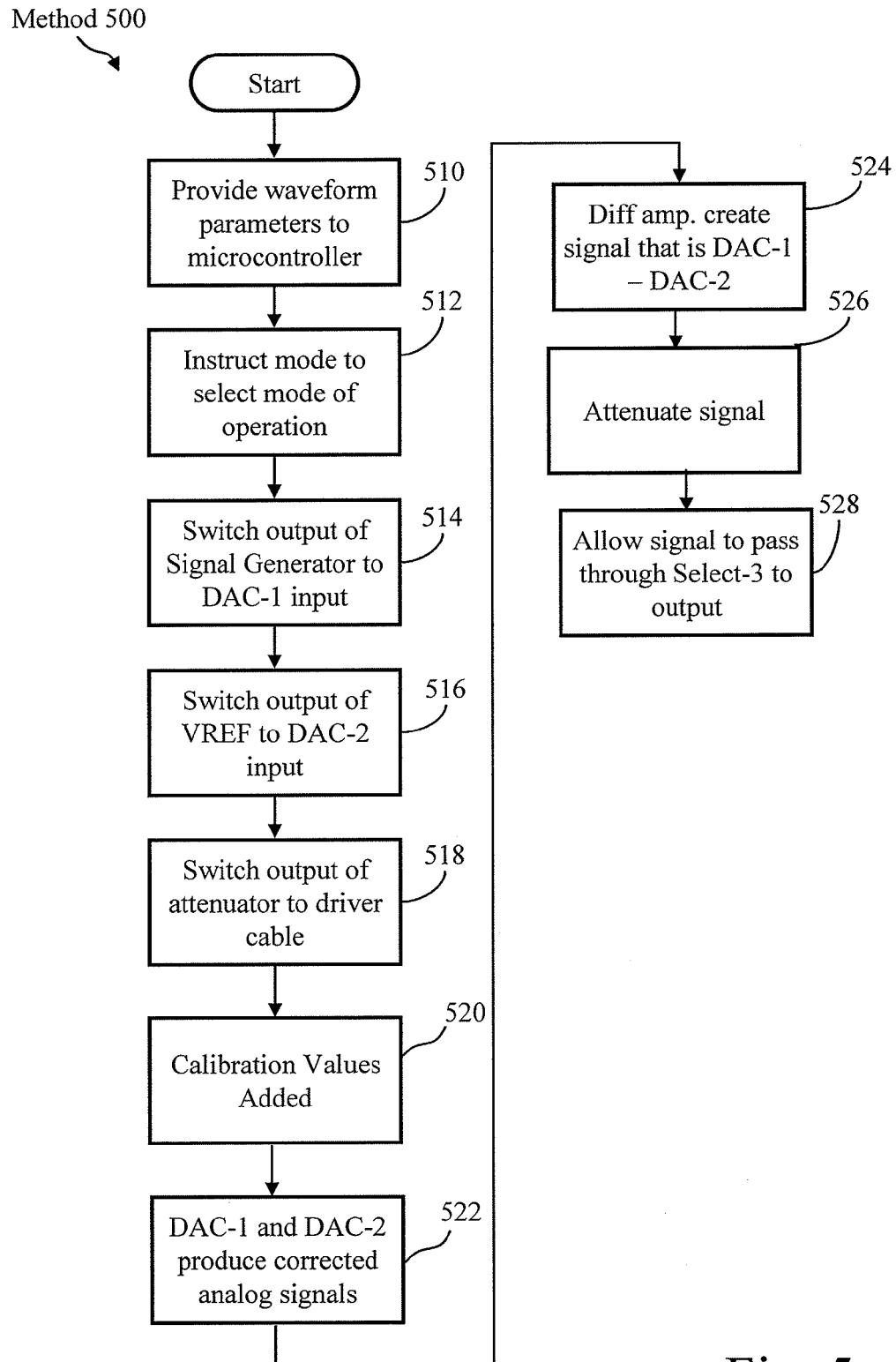
FIG. 5 is a flow diagram illustrating a method of driving the output device according to one embodiment of the present invention.

FIG. 5 is a flow diagram illustrating a method of driving the output device according to one embodiment of the present invention. In the steps that follow, according to one embodiment of the present invention, the driver 126 drives the output device 110. In one embodiment, the output device 110 is a coil assembly, and the driver 126 drives the output device 110 by energizing the coils of the coil assembly to precisely and accurately produce a magnetic field.

Step 510: Providing Waveform Parameters to Microcontroller:

In one embodiment, one or more waveform parameters may be provided. The waveform parameters may be provided to the microcontroller 234. In some embodiments, processor 114 provides the waveform parameters. For example, in some embodiments, the processor 114 transmits signals comprising the compensated electric waveform parameters to the microcontroller 234 within the driver 126. Examples of the compensated electric waveform parameters may include waveform type (e.g., sinusoidal, square, sawtooth), amplitude (e.g., 0.032 micro-gauss, 0.017 micro-gauss, 0.075 micro-gauss) and frequency (e.g., 0.3 Hz, 0.8 Hz, 5 Hz, 10 Hz). This communication may take place via the communication cable 122. In other embodiments, the communication may take place via any communication means known in the art—wired and/or wireless. Next, the method 500 may proceed to step 512.

Step 512: Instructing Mode to Select Mode of Operation:

After receiving the compensated electric waveform parameters, in one embodiment, the mode of operation is selected. In some embodiments, the microcontroller 234, under control of the S/W 236 issues the commands to the mode 212. This communication may take place via the system bus 240. Next, the method 500 proceeds to step 514. In some embodiments, steps 514, and/or 516, and/or 518 may be performed simultaneously or substantially simultaneously. In further embodiments, steps 514, and/or 516, and/or 518 may be performed in a different order than the order listed below. Thus, the order listed below is merely one embodiment and is not intended to limit the scope of the disclosed invention.

Step 514: Switching Output of Signal Generator to DAC-1 Input:

After the mode of operation is selected, in one embodiment, the select-1 214 switches the output of the signal generator 210 to the input of the DAC-1 220. In some embodiments, the select-I is commanded to perform this step. In one embodiment, this command may be provided by the mode 212. Next, the method 500 may proceed to step 516.

Step 516: Switching Output of VREF to DAC-2 Input:

After the mode of operation is selected, in one embodiment, the select-2 218 switches the output of the VREF 216 to the input of DAC-2 222. In some embodiments, the select-2 is commanded to perform this step. In one embodiment, mode 212 may provide this command. Next, the method 500 may proceed to step 518.

Step 518: Switching Output of Attenuator to Driver Cable:

After the mode of operation is selected, in one embodiment, the select-3 230 switches the output of the attenuator 228 to the driver cable 124. In some embodiments, the select-3 is commanded to perform this step. In one embodiment, mode 212 may provide this command. Next, the method 500 may proceed to step 520.

Figure 6:
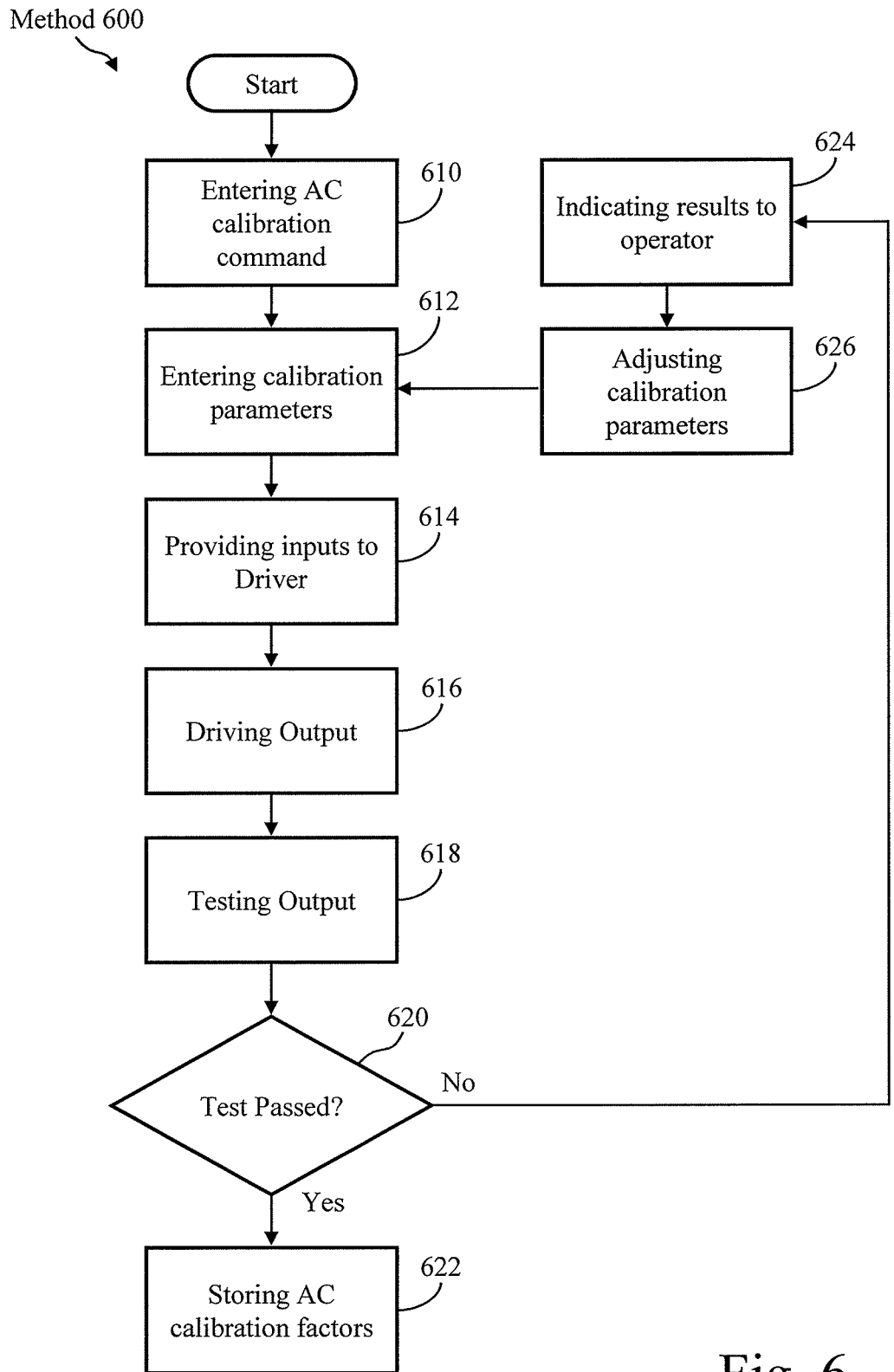
FIG. 6 is a flow diagram illustrating a method of AC calibration of the driver according to one embodiment of the present invention.
Figure 7:
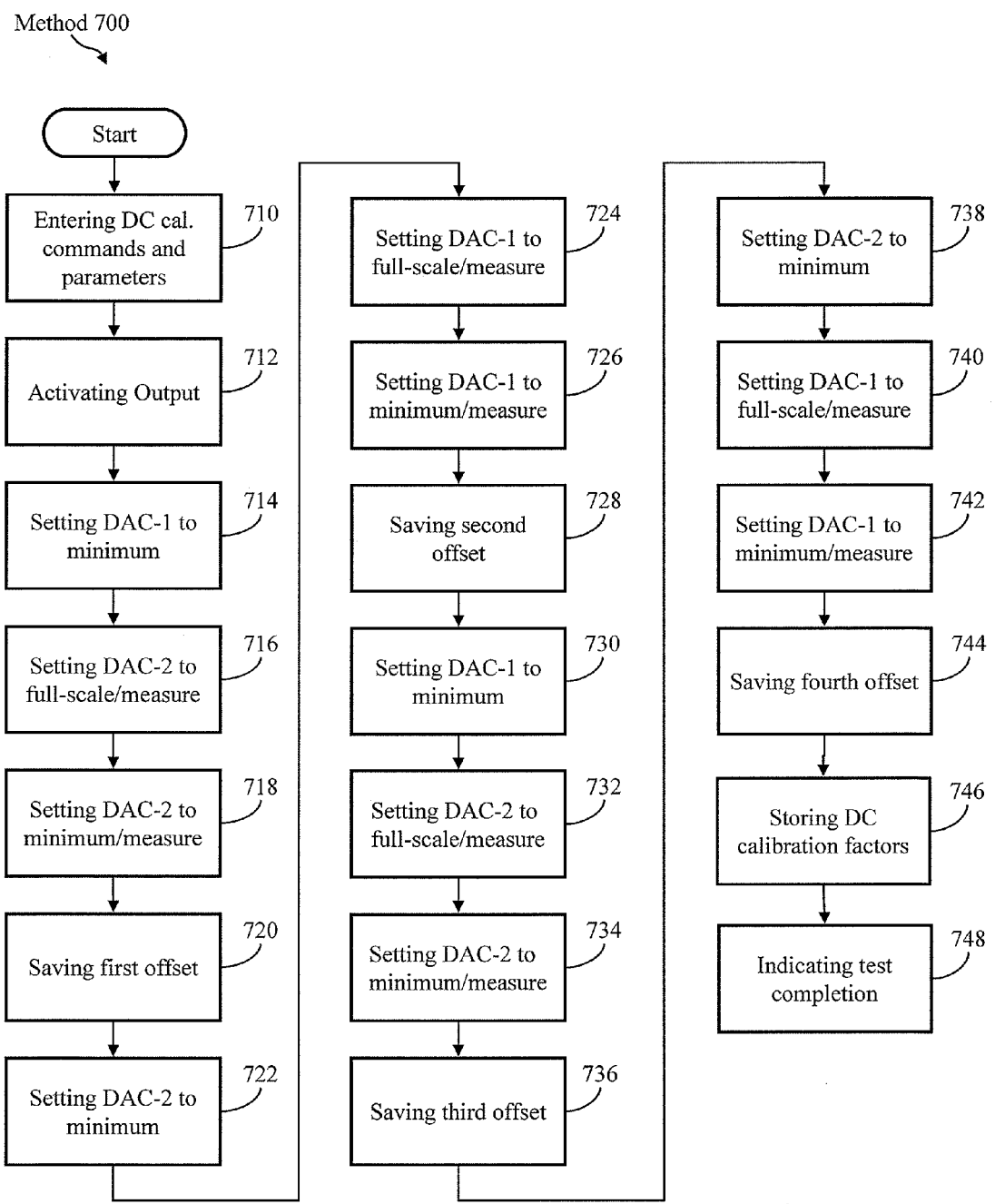
FIG. 7 is a flow diagram illustrating a method of DC calibration of the driver according to one embodiment of the present invention.

Step 520: Adding Calibration Values:

In one embodiment, after the mode performs the tasks described in steps 514, 516, 518, calibration values are added, such as those computed by the methods depicted in FIGS. 6 and 7 and described in methods 600 and 700, and/or other correction factors such as those that compensate for the ambient magnetic field. These calibration values may be used as correction factors in order to produce a precise and accurate signal. The method may next proceed to step 522

Step 522: Instructing DAC-1 and DAC-2 to Produce Corrected Analog Signals:

In one embodiment, after the calibration values are added, the signals provided by the DAC-1 220 and DAC-2 222 are compensated using the correction factors. In some embodiments, these commands are provided by the microcontroller 234, under control of the S/W 236. As explained herein, using the correction factors may allow embodiments of the invention to provide highly accurate and precise magnetic fields while reducing errors. Next, the method 500 may proceed to step 524.

Step 524: Creating a Signal:

In one embodiment, the differential amplifier 224 continuously creates a signal that is the difference between the output of the DAC-1 220 and the DAC-2 222. In some embodiments, the differential amplifier 224 outputs this signal to the attenuator 228. Next, the method 500 may proceed to step 526.

Step 526: Attenuate the Signal:

In one embodiment, the attenuator 228 receives the signal output from the differential amplifier 224. After receiving the signal output, in some embodiments, the attenuator 228 reduces the power of the signal. The attenuator 228 may reduce the power of the signal over a range of 1:1 (or unity) to $1:1 \times 10^{-15}$. Next, the method 500 may proceed to step 528.

Step 528: Allow Signal to Pass to be Output:

After the signal passes through the attenuator as described in step 524, in one embodiment, the attenuator transmits the signal to select-3 230. In a further embodiment, the select-3 230 allows the signal to be output. In one embodiment, the select-3 230 passes the signal to the driver cable 124. As a result, the output of the driver 126 may drive the driver cable 124. In some embodiments, the driver cable 124 is electrically connected to the input of the parallel combination of the compensation network and the output device 110. In some embodiments, the driver cable 124 thereby drives the output device 110.

As explained herein, a need exists for providing precise and accurate magnetic fields while minimizing the presence of errors. As further explained above, embodiments of the present invention address this need in a number of ways. One way in which the present invention address this need is using correction factors to control the amount of current that the driver 126 delivers. Thus, a need exists to determine the correction factors. Embodiments of the present invention meet this need by means of performing AC calibration, as described below.

One embodiment of the invention includes a method of AC calibration. The AC calibration method may include providing a signal as output, which is attenuated a number of times through a number of steps. After each step, the output may be tested to determine the offset values of the digital to analog converter devices (DAC-1 220 and DAC-2 222). After progressing through the steps, the method may determine whether the test has passed. According to one embodiment, if the test passed, then the AC calibration factors may be calculated and stored; if the test is not passed, then the AC calibration factors may be adjusted and the above-described steps may be repeated.

Various types of calibration may be performed by certain embodiments of the present invention. In some embodiments of the present invention, a method of AC calibration of driver for a magnetic field generating device comprises: receiving an AC calibration level; directing the driver to produce an output signal; measuring the output signal; and comparing the measured output signal to an expected value.

In some embodiments, the method of AC calibration of a driver for a magnetic field generating device may further comprise determining and storing an AC calibration factor.

In some embodiments, the method of AC calibration of a driver for a magnetic field generating device may further comprises receiving a new AC calibration level; and using the new AC calibration level to further calibrate the driver.

In some embodiments, the method of AC calibration of a driver for a magnetic field generating device may further comprise determining a new AC calibration level, based at least in part on a sensor signal received from a sensor configured to measure the output signal.

In some embodiments of the present invention, directing the driver to produce an output signal comprises: transmitting a signal to an attenuator configured to produce an attenuated signal; and transmitting the attenuated signal to a dummy load.

In some embodiments of the present invention the AC calibration factor produces a linearized AC characteristic for the driver.

FIG. 6 is a flow diagram illustrating a method of AC calibration 300 of the driver 100 according to one embodiment of the present invention. As noted above, a need exists to minimize electronic errors due to non-linearity and stray AC offsets in the driver. In some embodiments, the process of the method 600 minimizes electronic errors due to stray AC offsets in the driver.

In general, according to one embodiment, the method 600 comprises providing and testing a number of attenuated signals. In one embodiment, calibration parameters are computed based on these tests. If the test is passed, the calibration parameters are saved. If the test is not passed, then the steps of providing and testing the attenuated signals may be executed again. This process may continue iteratively until the test is passed. In one embodiment, the method 600 includes the following steps:

Step 610: Entering AC Calibration Command:

In one embodiment, the AC calibration process is initiated. In some embodiments, an operator enters a command to begin AC calibration. For example, the operator may enter the command using the processor 114. In one embodiment, the operator enters the command via the user interface communicatively connected to processor 114. Next, the method 600 may proceed to step 612.

Step 612: Entering Calibration Parameters:

In one embodiment, desired calibration levels are provided. In some embodiments, the operator enters desired calibration levels (e.g., voltage, current, frequency values). For example, the operator may enter the calibration levels using the processor 114. In one embodiment, the operator enters the calibration levels via a user interface communicatively connected to processor 114. In a further embodiment the calibration levels are provided without the need for operator intervention, for example, the calibration levels may be stored on a computer readable medium accessed by the processor 114. Next, the method 600 may proceed to step 614.

Step 614: Providing Inputs to Driver:

In one embodiment, commands and/or other inputs are provided to the driver 126. In some embodiments, the processor 114 may transmit signal comprising one or more commands to the microcontroller. For example, these signals may comprise commands to begin AC calibration and/or the AC calibration levels. In certain embodiments, the signals are transmitted via the communication cable 122. In other embodiments, the signals are transmitted via any communication means known in the art—wired and/or wireless. Next, the method 600 may proceed to step 616.

Step 616: Driving Output:

In one embodiment, the output of the driver 126 is activated for AC calibration. In general, according to one embodiment, the differential amplifier 224 provides a signal to the attenuator 228, which attenuates the signal a specified number of times. After each attenuation step, the attenuator 228 may provide the attenuated signal to the dummy load 232 so that the output can be measured.

More specifically, for AC calibration according to one embodiment, the microcontroller 234, under control of the S/W 236, commands the mode 212, via the system bus 240 to select the AC calibration mode of operation. After receiving the command, the mode 212, may set the select-1 214 to switch the output of the signal generator 210 to the input of the DAC-1 220. In one embodiment, the mode 212 may set the select-2 218 to switch the VREF 216 to the input of the DAC-2 222. In a further embodiment, the mode 212 may set the select-3 230 to pass the output of the attenuator 228 to the dummy load 232. In one embodiment, the microcontroller 234, under control of the S/W 236, commands the DAC-1 220 and the DAC-2 222 to output a signal in a range of 0.1 Vpp to 1 Vpp. The differential amplifier 224 may continuously create a signal that is the difference between the output of the DAC-1 220 and the DAC-2 222.

In one embodiment, the differential amplifier 224 may output this signal to the attenuator 228. In one embodiment, the attenuator 228, which is under the control of the S/W 236, sequentially steps the attenuation of the signal over a range of 1:1 (or unity) to 1:10000. In some embodiments, the number of steps is five or six, but various embodiments are capable of performing any number of steps. In one embodiment, after the signal is attenuated by the attenuator 228, the attenuated signal is passed by the select-3 230 to the dummy load 232. In one embodiment, the dummy load 232 allows direct measurement of the output. Next, the method 600 may proceed to step 618.

Step 618: Testing Output:

In one embodiment, the output of the driver 126 is tested. In some embodiments, the operator tests the output of the driver 126. In some embodiments, the output tested includes voltage and/or frequency. In some embodiments, the output is tested at the contact points of coil cables 124. In some embodiments, the operator tests the output with a digital multimeter to determine the offset values of DAC-1 220 and DAC-2 222 corresponding to the discrete values in the range of 0.1 Vpp to 1 Vpp described in step 616. In one embodiment, the results of the tested output are used to calculate the offset values. For a given value provided to DAC-1 and DAC-2, the resultant output is measured and used in a calculation to generate the offset and scale coefficients. In one embodiment, the output resulting from DAC-1 set at full scale and DAC-2 at minimum is compared to the output resulting from DAC-2 set at full scale and DAC-1 at minimum. In one embodiment, when DAC-1 is at full scale, the output is an AC value varying between zero and a voltage peak. This peak value may be measured and compared to a steady state value provided by DAC-2. The difference between the two values should be zero.

In one embodiment, variations in output from DAC-1 and/or DAC-2 may be corrected by using the offset and scale adjustment values in the following linear equation: new value=$\{(X_0-X_1)*[\text{old value}]+[\text{measured offset}]\}$. In the preceding linear equation, $X_0$ and $X_1$ may be determined from the measured output of DAC-1 and DAC-2. In one embodiment, a difference equation is used to calculate the values of $X_0$ and $X_1$. The difference equation may include the slope and offset of the difference of the minimum and full-scale values from DAC-1 and DAC-2. Specifically, in one embodiment $X_0$ is the corrected minimum value determined by applying the difference equation from DAC-1 and DAC-2 to each DAC value. In one embodiment $X_1$ is the corrected full-scale value determined by applying the difference equation from DAC-1 and DAC-2 to each DAC value. The measured offset is a calculation comparing the DAC-1 minimum to the DAC-2 minimum and the DAC-1 full-scale to the DAC-2 full-scale. Once the scale and offset factors are generated, they are tested to ensure that the waveform is centered around zero within a measurement variance. In a further embodiment, an automated process tests the output of the driver 126, thus eliminating the need for operator intervention. Next, the method 600 may proceed to step 620.

Step 620: Test Passed?:

In one embodiment, the method 600 determines whether the test has passed. In one embodiment, the operator manually enters the resultant values from step 618 (e.g., voltage and frequency) into the processor 114 via a user interface. The offset and scale calibration values may be tested to determine compliance to the output voltage specifications within some measurement window. For example, if code values sent to DAC-1 220 and DAC-2 222 should result in a 0.8431 Vpp value, with a zero offset, this may be measured at the output of the differential amplifier 224 and verified within specifications. In one embodiment, the output measurement at the test point will be within ±0.000025V of the determined value, as determined by an HP3457A, with a 25 sample integration. This type of test may be performed across a range of values for DAC-1 220, DAC-2 222, and/or the differential amplifier 224. This test may ensure that the relationship between a code value and an output voltage is correct over the entire output range.

In one embodiment, after the electronics are calibrated, the system 100 may be tested and calibrated to ensure the magnetic field at the point of use is within specification. The system may apply a drive signal to the coils. A sensitive magnetometer may measure the magnetic field strength, which is then compared to the expected magnetic field strength. As the relationship between code values and signal drive output has been previously established and calibrated, a simple scale factor adjustment may be used to ensure the magnetic field is within specifications across the range of use.

System software of the processor 114 may determine if the test has passed. If yes (test passed), then the method 600 proceeds to step 622. If no (test not passed), then the method 600 may proceed to step 626.

Step 622: Storing AC Calibration Factors:

In one embodiment, AC calibration factors that produce a linearized AC characteristic for the driver 126 are calculated. In some embodiments, the AC calibration factors are not stored, and step 622 is omitted. In one embodiment, the processor 114 transmits signals comprising the AC calibration parameters to the microcontroller 234. In some embodiments, the processor transmits these signals via the communication cable 122. In some embodiments, the microcontroller 234 under control of the S/W 236, then stores the AC calibration factors in its non-volatile memory (not shown). In some embodiments, the completion of AC calibration is communicated. For example, in one embodiment, the processor 114, under control of system software, then communicates the completion of AC calibration to the operator. In one embodiment, this communication is performed via a display which is communicatively connected to the processor 114.

Step 624: Indicating Results to Operator:

In one embodiment, if AC calibration fails in step 620, the failure of AC calibration is communicated. In one embodiment, the processor 114 communicates the failure of the AC calibration. In one embodiment, this information may be communicated to a display which is communicatively connected to the processor 114. In some embodiments, the measurements taken in step 620 are communicated to the microcontroller 234. In some embodiments, this communication takes place via the communications cable 122. Next, the method 600 may proceed to step 626.

Step 626: Adjusting Calibration Parameters:

In one embodiment, new calibration levels are calculated. In some embodiments, these calibration levels are based, at least in part, on the measurements taken in step 620. In some embodiments, the processor 114, under control of system software, calculates the calibration levels. In a further embodiment, the processor 114 transmits signals comprising the calibration levels. In a further embodiment, the calibration levels are communicated via a display which is communicatively connected to the processor 114. Next, the method 600 may return to step 612.

As explained above, a need exists for providing precise and accurate magnetic fields while minimizing the presence of errors. As further explained above, embodiments of the present invention address this need in a number of ways. One way in which the need is addressed is by using correction factors to control the amount of current provided by the driver 126. Thus, a need exists to determine the correction factors. Embodiments of the present invention meet this need by means of performing DC calibration, as described below.

One embodiment includes a DC calibration method. A method for DC calibration of a driver for a magnetic field generating device may comprise: receiving DC calibration levels; directing the driver to produce an output signal; measuring the output signal; and determining and storing an offset, based at least in part on the measurement of the output signal.

In some embodiments of a method for DC calibration of a driver for a magnetic field generating device, determining an offset may comprise: setting a first digital to analog converter to produce minimum output; setting a second digital to analog converter to produce full-scale output and measuring the driver's output signal; setting the second digital to analog converter to produce minimum output and measuring the driver's output signal; and determining an offset based at least in part on the measurements of the driver's output signal.

In some embodiments of a method for DC calibration of a driver for a magnetic field generating device, directing the driver to produce an output signal may comprise: transmitting a signal to an attenuator configured to produce an attenuated signal; and transmitting the attenuated signal to a dummy load.

In some embodiments of a method for DC calibration of a driver for a magnetic field generating device, determining and storing an offset comprises determining and storing more than one offset, and wherein determining each offset comprises setting one digital to analog converter to minimum output and another digital to analog converter to full-scale output. In some embodiments of a method for DC calibration of a driver, determining and storing more than one offset comprises determining and storing four offsets. In some embodiments of a method for DC calibration of a driver, determining a DC calibration factor comprises combining the four offsets.

FIG. 7 is a flow diagram illustrating a method of DC calibration 700 of the driver 126 according to one embodiment of the present invention. As noted above, a need exists to minimize electronic errors due to non-linearity and stray DC offsets in the driver. Embodiments of the present invention meet this need. In one embodiment, the process of method 700 may minimize electronic errors due to non-linearity and DC offsets in the driver. The method 700 includes the following steps:

Step 710: Entering DC Calibration Command and Parameters:

In one embodiment, a command to begin DC calibration is provided. In some embodiments, DC calibration parameters are also provided. In one embodiment, an operator enters the DC calibration command using the processor 114. In a further embodiment, the operator also enters DC calibration parameters using the processor 114. These communications may be entered via a user interface which is communicatively connected to the processor 114. In one embodiment, the processor 114 transmits signals comprising the DC calibration command and DC calibration levels to the microcontroller 234. In a further embodiment, this communication takes place via the communication cable 122. Next, the method 700 may proceed to step 712.

Step 712: Activating Output:

In one embodiment, the output of the driver 126 is activated for DC calibration. In general, according to one embodiment, the differential amplifier 224 transmits a signal to the attenuator 228, which attenuates the signal. After performing this step, the attenuator 228 transmits the attenuated signal to the dummy load 232 so that the output can be measured.

More specifically, for DC calibration in one embodiment, the microcontroller 234, under control of the S/W 236, commands the mode 212, via the system bus 240 to select the DC calibration mode of operation. After receiving the command, the mode 212 may set the select-1 214 to switch the VREF 216 to the input of the DAC-1 220. In one embodiment, the mode 212 may set the select-2 218 to switch ground to the input of the DAC-2 222. In one embodiment, the mode 212 may set the select-3 230 to pass the output of the attenuator 228 to the dummy load 232. The differential amplifier 224 may continuously transmit a signal that is the difference between the signal output by DAC-1 220 and DAC-2 222. In one embodiment, the differential amplifier 224 may output this signal to the attenuator 228, which under the control of the S/W 236, attenuates the signal over a range of 1:1 (or unity) to $1:1\times10^{-15}$ for calibration. Also, the attenuator level may be set from 1:1 to 1:10000, to allow direct measurement of the output. In one embodiment, the attenuated signal is passed by the select-3 230 to the dummy load 232. Next, the method 700 may proceed to step 714.

Step 714: Setting DAC-1 to Minimum:

In one embodiment, the DAC-1 220 is set to minimum output. In a further embodiment, the microcontroller 234, under control of the S/W 236, commands the DAC-1 220 to minimum output. Next, the method 700 may proceed to step 716.

Step 716: Setting DAC-2 to Full-Scale/Measure:

In one embodiment, the DAC-2 222 is set to full-scale output. In a further embodiment, the microcontroller 234, under control of the S/W 236, commands the DAC-2 222 to full-scale output. After the DAC-2 222 is set to full-scale output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement at the processor 114. In some embodiments, this entry is performed via the user interface of the processor 114. In a further embodiment, a process tests the output of the driver 126 without the need for operator intervention. Next, the method 700 may proceed to step 718.

Step 718: Setting DAC-2 to Minimum/Measure:

In one embodiment, the DAC-2 is set to minimum output. In a further embodiment, the microcontroller 234, under control of the S/W 236, commands the DAC-2 222 to minimum output. After the DAC-2 222 is set to minimum output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement at the processor 114. In some embodiments, this entry is performed via the user interface communicatively connected to the processor 114. In a further embodiment, a process tests the output of the driver 126 without the need for operator intervention. Next, the method 700 may proceed to step 720.

Step 720: Saving First Offset:

In one embodiment the first offset is computed and saved. In some embodiments, the first offset is computed by the processor 114, under control of system software. After the first offset is computed, in some embodiments the processor 114 saves the first offset in a data store which is communicatively connected to the processor 114. Next, the method 700 may proceed to step 722.

Step 722: Setting DAC-2 to Minimum:

In one embodiment, the DAC-2 222 is set to minimum output. In a further embodiment, the microcontroller 234, under control of the S/W 236, commands the DAC-2 222 to minimum output. Next, the method 700 may proceed to step 724.

Step 724: Setting DAC-1 to Full-Scale/Measure:

In one embodiment, the DAC-2 222 is set to full-scale output. In a further embodiment, the microcontroller 234, under control of the S/W 236, commands the DAC-1 220 to full-scale output. After the DAC-1 222 is set to full-scale output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement at the processor 114. In some embodiments, this entry is performed via the user interface of the processor 114. In a further embodiment, a process tests the output of the driver 126 without the need for operator intervention. Next, the method 700 may proceed to step 726.

Step 726: Setting DAC-1 to Minimum/Measure:

In one embodiment, the DAC-1 is set to minimum output. In a further embodiment, the microcontroller 234, under control of the S/W 236, commands the DAC-1 222 to minimum output. After the DAC-1 222 is set to minimum output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement at the processor 114. In some embodiments, this entry is performed via the user interface of the processor 114. In a further embodiment, a process tests the output of the driver 126 without the need for operator intervention. Next, the method 700 may proceed to step 728.

Step 728: Saving Second Offset:

In one embodiment the second offset is computed and saved. In some embodiments, the second offset is computed by the processor 114, under control of system software. After the second offset is computed, in some embodiments the processor 114 saves the second offset in a data store which is communicatively connected to the processor 114. Next, the method 700 proceeds to step 730.

Step 730: Setting DAC-1 to Minimum:

In one embodiment, the DAC-1 220 is set to minimum output. In a further embodiment, the microcontroller 234, under control of the S/W 236, commands the DAC-1 220 to minimum output. Next, the method 700 may proceed to step 732.

Step 732: Setting DAC-2 to Full-Scale/Measure:

In one embodiment, the DAC-2 222 is set to full-scale output. In a further embodiment, the microcontroller 234, under control of the S/W 236, commands the DAC-2 222 to full-scale output. After the DAC-2 222 is set to full-scale output, in some embodiments the operator tests the output of the driver 126. The test(s) may be for the voltage or any other properties that can be measured. In one embodiment, the operator tests the output at the contact points of the coil cables 124 with a digital multimeter. In a further embodiment, the operator enters the resultant measurement via a user interface communicatively connected to the processor 114. In a further embodiment, a process tests the output of the driver 126 without the need for operator intervention. Next, the method 700 may proceed to step 734.

Step 734: Setting DAC-2 to Minimum/Measure:

In one embodiment, the DAC-2 is set to minimum output. In a further embodiment, the microcontroller 234, under control of the S/W 236, commands the DAC-2 222 to minimum output. After the DAC-2 222 is set to minimum output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement at the processor 114. In some embodiments, this entry is performed via the user interface of the processor 114. In a further embodiment, a process tests the output of the driver 126 without the need for operator intervention. Next, the method 700 may proceed to step 736.

Step 736: Saving Third Offset:

In one embodiment the third offset is computed and saved. In some embodiments, processor 114 computes the third offset. After the third offset is computed, in some embodiments the processor 114 saves the third offset to a data store which is communicatively connected to processor 114. Next, the method 700 may proceed to step 738.

Step 738: Setting DAC-2 to Minimum:

In one embodiment, the DAC-2 222 is set to minimum output. In a further embodiment, the microcontroller 234, under control of the S/W 236, commands the DAC-2 222 to minimum output. Next, the method 700 may proceed to step 740.

Step 740: Setting DAC-1 to Full Scale/Measure:

In one embodiment, the DAC-1 220 is set to full-scale output. In a further embodiment, the microcontroller 234, under control of the S/W 236, commands the DAC-1 220 to full-scale output. After the DAC-1 220 is set to full-scale output, in some embodiments the operator tests the output of the driver 126. The test(s) may be for the voltage or any other properties that can be measured. In one embodiment, the operator tests the output at the contact points of the output device 124 with a digital multimeter. In a further embodiment, the operator enters the resultant measurement via a user interface communicatively connected to the processor 114. In a further embodiment, a process tests the output of the driver 126 without the need for operator intervention. Next, the method 700 may proceed to step 742.

Step 742: Setting DAC-1 to Minimum/Measure:

In one embodiment, the DAC-1 is set to minimum output. In a further embodiment, the microcontroller 234, under control of the S/W 236, commands the DAC-1 220 to minimum output. After the DAC-1 220 is set to minimum output, in some embodiments the operator tests the output of the driver 126. The test(s) may be for the voltage or any other properties that can be measured. In one embodiment, the operator tests the output at the contact points of the coil cables 124 with a digital multimeter. In a further embodiment, the operator enters the resultant measurement via a user interface communicatively connected to the processor 114. In a further embodiment, a process tests the output of the driver 126 without the need for operator intervention. Next, the method 700 may proceed to step 744.

Step 744: Saving Fourth Offset:

In one embodiment, the fourth offset is computed and saved. In some embodiments, processor 114 determines the fourth offset. After determining the fourth offset, in some embodiments the processor 114 saves the fourth offset in a data store which is communicatively connected to the processor 114. Next, the method 700 may proceed to step 746.

Step 746: Storing DC Calibration Factors:

In one embodiment, the DC calibration factors are calculated and stored. In some embodiments, the offsets captured and saved by the previous steps are combined under algorithmic control to produce DC calibration factors. The DC calibration factors may produce a linearized DC characteristic for the driver 126. For example, in some embodiments, the processor 114 may calculate the DC calibration factors. In a further embodiment, the processor 114 produces a linearized DC characteristic for the driver 126. Also, the processor 114 may store the linearized DC characteristic in the nonvolatile memory of the processor 114. In one embodiment, the processor 114 communicates the DC calibration parameters to the microcontroller 234 within the driver 126. This communication may take place via the communication cable 122. In some embodiments, the microcontroller 234 under control of the S/W 236, may store the DC calibration factors in a data store which is communicatively connected to microcontroller 234. Next, the method 700 may proceed to step 748.

Step 748: Indicating Test Completion:

In one embodiment, test completion is indicated. In some embodiments, the processor 114 performs this step. For example, in some embodiments, the processor 114 communicates the completion of DC calibration via the communication cable 122. In a further embodiment, the processor 114 may cause the CD calibration test complete status to be displayed on the display which is communicatively connected to the processor 114. Next, the method 700 ends.

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

We claim:

1. A driver for a magnetic field generating device comprising:
    a programmable signal generator configured to receive a control signal from a processor, and based on the control signal, output a driver signal;
    a first digital to analog converter configured to receive the driver signal and output a first output signal;
    a second digital to analog converter configured to receive the driver signal and output a second output signal;
    a differential amplifier configured to receive the first output signal and the second output signal and output a third signal;
    an attenuator configured to receive the third signal and output a fourth signal; and
    one or more coils configured to receive the fourth signal and generate a magnetic field to provide a magnetic resonance treatment to a subject.

2. The driver of claim 1, wherein the processor is configured to receive the first and second signals and calibrate the signal generator based on the first and second signals.

3. The driver of claim 1, further comprising at least one relay device connected to at least one of the first or second digital to analog converters.

4. The driver of claim 3, further comprising a voltage reference source connected to the at least one relay device.

5. The driver of claim 4, wherein the at least one relay device is used to relay output from the voltage reference source to the second digital to analog converter.

6. The driver of claim 3, wherein the signal generator is coupled to the at least one relay device.

7. The driver of claim 6, wherein the at least one relay device is used to relay output from the signal generator to the first digital to analog converter.

8. The driver of claim 1, further comprising at least one sensor configured to monitor physical parameters of the subject receiving the magnetic field.

9. The driver of claim 8, wherein the sensor comprises one or more of: an EGK, an EEG, a heart rate monitor, or a blood pressure monitor.

10. The driver of claim 1, further comprising a magnetometer.

11. The driver of claim 10, wherein the magnetometer is configured to sense an ambient magnetic field.

12. The driver of claim 1, wherein the signal generator comprises a low noise, low frequency, sinusoidal signal generator.

13. The driver of claim 1, wherein the control signal comprises one or more waveform parameters.

14. The driver of claim 13, wherein the one or more waveform parameters comprise one or more of frequency and waveform type.

15. The driver of claim 1, wherein the subject comprises a human.

* * * * *